(12) United States Patent
Baehrecke et al.

(10) Patent No.: US 7,838,645 B2
(45) Date of Patent: Nov. 23, 2010

(54) FUNCTION OF AUTOPHAGY GENES IN CELL DEATH

(75) Inventors: Eric H. Baehrecke, University Park, MD (US); Ajjai Alva, Baltimore, MD (US); Michael J. Lenardo, Potomac, MD (US); Yu Li, Rockville, MD (US)

(73) Assignees: University of Maryland College Park, College Park, MD (US); National Institutes of Health, Bethesda, MD (US)

( * ) Notice: Subject to any disclaimer, the term of this patent is extended or adjusted under 35 U.S.C. 154(b) by 0 days.

(21) Appl. No.: 11/119,569

(22) Filed: May 2, 2005

(65) Prior Publication Data

US 2005/0276809 A1    Dec. 15, 2005

Related U.S. Application Data

(60) Provisional application No. 60/566,857, filed on Apr. 30, 2004.

(51) Int. Cl.
*C07H 21/02* (2006.01)
*C07K 16/00* (2006.01)

(52) U.S. Cl. .................................. 536/23.1; 530/387.1

(58) Field of Classification Search ........................ None
See application file for complete search history.

(56) References Cited

U.S. PATENT DOCUMENTS 5,837,837 A * 11/1998 Hunter et al. .............. 536/23.1

FOREIGN PATENT DOCUMENTS

WO    WO 03/020767 A2 *    3/2003

OTHER PUBLICATIONS

Serazin-Leroy (Am J Physiol Endoconol Metab, 2000, 279:E1398-E1405).*
Verma et al. (Nature 1997, 389: 239-242).*
Amalfitano et al. (Current Gene Therapy 2002, 2: 111-133).*
Pandha et al. (Current Opinion in Investigational Drugs 2000; 1 (1): abstract).*
McNeish et al (Gene Therapy, 2004, 11:497-503).*
Burgess et al. (J. Cell Biol. 111:2129-2138, 1990).*
Lazar et al. ( Mol. Cell Biol. 8:1247-1252, 1998).*
Christiansen et al (Mol Cancer Ther, 2004, 3:1493-1501).*
Topp et al (Journal of Controlled Release, 1998, 53:15-23).*
Pandha et al. (Current Opinion in Investigational Drugs 2000; 1 (1): 122-134).*
McCormick (Nature Reviews, 2001, 1:130-141).*
Berry et al (Autophagy, Apr. 2008, 1;4(3):359-360).*
Berry et al (Cell, Dec. 2007, 14;131(6): 1137-1148).*
A. Degterev, M. Boyce, J. Yuan, *Oncogene* 22, 8543-67 (2003).
D. W. Nicholson, N. A. Thornberry, *Science* 299, 214-5 (2003).
A. Strasser, L. O'Connor, V. M. Dixit, *Annual Review of Biochemistry* 69, 217-45 (2000).
M. Leist, M. Jaattela, *Nature Reviews Molecular Cell Biology* 2, 589-98 (2001).
F.K. Chan, J. Shisler, J.G. Bixby, M. Felices, L. Zheng, M. Appel, J. Orenstein, B. Moss, M.J. Lenardo, *J Biol Chem.* 278, 51613-21 (2003).
N. Holler et al., *Nature Immunology* 1, 489-95 (2000).
Y. Ohsumi, *Nature Reviews Molecular Cell Biology* 2, 211-6 (2001).
D. J. Klionsky, S. D. Emr, *Science* 290, 1717-21 (2000).
E. H. Baehrecke, *Nature Reviews Molecular Cell Biology* 3, 779-87 (2002).
W. Fiers, R. Beyaert, W. Declercq, P. Vandenabeele, *Oncogene* 18, 7719-30 (1999).
S.M. Gorski, et al. *Current Biology* 13, 358-63 (2003).
C. Y. Lee et al., *Current Biology* 13, 350-7 (2003).
L. Jia et al., *British Journal of Haematology* 98, 673-85 (1997).
I. Tanida, N. Mizushima, M. Kiyooka, M. Ohsumi, T. Ueno, Y. Ohsumi, E. Kominami, *Mol Biol Cell.* 10, 1367-79 (1999).
J. Kim, V.M. Dalton, K.P. Eggerton, S.V. Scott, D.J. Klionsky, *Mol Biol Cell.* 10, 1337-51 (1999).
X. H. Lianget et al., *Journal of Virology* 72, 8586-96 (1998).
X. H. Liang et al., *Nature* 402, 672-6 (1999).
Z. Yue, S. Jin, C. Yang, A. J. Levine, N. Heintz, *Proceedings of the National Academy of Sciences of the United States of America* 100, 15077-82 (2003).
X. Qu et al., *J Clin Invest.* 112, 1809-20 (2003).
A. Devin, Y. Lin, Z.G. Liu, *EMBO Rep.* 4, 623-7 (2003).
RW. Oppenheim, RA Flavell, S. Vinsant, et al., *J. Neutosci.* 21, 4752-60 (2001).
H. J. Chun et al, *Nature* 419, 395-9 (2002).28.
Y. Lin, A. Devin, Y. Rodriguez, Z. G. Liu, *Genes & Development* 13, 2514-26 (1999).
K.R. Mills, M. Reginato, J. Debnath, B. Queenan, J.S. Brugge, *Proceedings of the National Academy of Sciences of the United States of America* 101, 3438-43 (2003).
M. Li et al., *Science* 288, 335-9 (2000).
J. Yuan, M. Lipinski, A. Degterev, *Neuron* 40, 401-13 (2003).
B. Levine, DJ. Klionsky, *Dev. Cell* 6, 463-477 (2004).
M. Tsukada, Y. Ohsumi, *FEBS Letters* 333, 169-74 (1993).
M. Thumm, R. Egner, B. Koch, M. Schlumpherger, M. Straub, et al. *FEBS Letters* 349, 275-280 (1994).
M. Chautan, G. Chazal, F. Cecconi, P. Gruss, et al., *Curr. Biol.*, 9, 967-70 (1990).
T. M. Harding, Ka Morano, SV Scott, et al., *J. Cell Biol.* 131, 591-602 (1995).
DJ. Klionsky, JM Cregg, WAJ Dunn, SD Ernt, et al. *Dev Cell* 5, 539-45 (2003).

* cited by examiner

*Primary Examiner*—Sean E Aeder
(74) *Attorney, Agent, or Firm*—Kelly K. Reynolds; Steven J. Hultquist; Intellectual Property/Technology Law

(57) ABSTRACT

The present invention relates to a new molecular pathway in which activation of the receptor-interacting protein (RIP, a serine-threonine kinase) and Jun N-terminal kinase induce cell death with the morphology of autophagy. Further, autophagic death is induced by caspase 8 inhibition and expression of the mammalian genes ATG7 and beclin.

2 Claims, 21 Drawing Sheets

SEQUENCE LISTING

<160> NUMBER OF SEQ ID NOS: 21

<210> SEQ ID NO 1
<211> LENGTH: 3061
<212> TYPE: DNA
<213> ORGANISM: Mus musculus

<400> SEQUENCE: 1

```
gggggctgtg gttgccggaa gttgagcggc ggctggtaag aacagtagcc atggggggacc      60
ctggactggc caagttgcag ttcgccccct ttaatagtgc cctggacgtt ggcttctggc     120
acgaactgac ccagaagaag ttgaacgagt accgcctgga cgaggcaccc aaagacatca     180
agggctatta ctacaatggt gactctgctg gtctgcccac ccgcttgacg ttggagttca     240
gtgcttttga catgagtgcc tccacgcctg cccactgctg cccggccatg ggaaccctgc     300
acaacaccaa cacacttgag gcttttaaga cagcagacaa gaagctcctt ctggagcagt     360
cagcaaatga gatctgggaa gccataaagt caggtgctgc tctcgaaaac cccatgctcc     420
tcaacaagtt tctgctcctg accttcgcgg acctaaagaa gtaccacttc tactactggt     480
tttgctgccc cgccctctgt cttcctgaga gcatccctct aatccgggga cctgtgagct     540
tggatcaaag gctttcacca aaacagatcc aggccctgga gcatgcctat gatgatctgt     600
gtcgagccga aggcgtcacg gccctgccct acttcttatt caagtacgat gacgacactg     660
ttctggtctc cttgctcaaa cactacagtg atttcttcca aggtcaaagg acaaagataa     720
cagttggtgt gtacgatccc tgtaacctag cccagtaccc tggatggcct ttgaggaatt     780
ttttggtcct ggcagcccac agatggagcg gcagtttcca gtccgttgaa gtcctctgct     840
ttcgggaccg caccatgcag ggagctagag acgtgacaca tagcatcatc tttgaagtga     900
aacttccaga aatggcattt agcccagatt gtcctaaagc tgttggctgg gagaagaacc     960
agaaaggagg catgggtccg aggatggtga acctcagtgg atgtatggac cccaaaaggc    1020
tggctgagtc atctgtggat ctgaatctca agctgatgtg ctggcgattg gtccccacct    1080
tggacttgga caaggtcgtg tctgtcaagt gcctgctgct gggagctggt accttggggt    1140
gtaatgtggc taggacactg atgggctggg gcgtcagaca tgtcaccttt gtggataacg    1200
ccaagatctc ctactccaat cccgtgaggc agcctctgta tgaatttgaa gattgtctag    1260
ggggtggcaa gcccaaggcc ctggctgcag cagagcggct acagaaaata tttcccggag    1320
tgaatgccag agggttcaac atgagcatcc ccatgccagg acaccctgtg aacttctctg    1380
acgtcacgat ggagcaggcc cgcagagatg tggagcagct ggagcagctc attgataacc    1440
atgatgtcat cttcctgcta atggacacca gggagagccg gtggcttcct actgttattg    1500
cagccagcaa gcgaaagctg gtcatcaacg ctgccttggg gtttgatacc tttgttgtca    1560
tgagacatgg cctgaagaaa cccagcagc agggagccgg agacctctgc ccaagccatc    1620
ttgtagcacc tgctgacctg ggctcctcac tttttgccaa catccctgga tacaagcttg    1680
gctgctactt ctgcaatgat gtggtggctc caggagattc aaccagagac cggactctgg    1740
```

```
accagcagtg cacagtgagc cgcccaggcc tggccgtgat tgcaggtgcc ctggctgtgg   1800
agctgatggt ctctgtcctg cagcatcctg agggggggcta cgccatcgcc agcagcagtg   1860
atgaccgcat gaatgagcct cccacctcgc tgggacttgt gcctcaccag atccggggtt   1920
ttctgtcacg gttcgataat gttcttcctg tcagcctggc atttgataaa tgtacagcct   1980
gttcacccaa agttcttgat cagtacgagc gagaaggatt caccttccta gcgaaggttt   2040
ttaactcctc acattccttc ttagaagact tgaccggtct taccctgctc catcaagaga   2100
cccaagctgc tgagatctgg gacatgagtg acgaggagac tgtctgaagc aagcaaccac   2160
agctcaggag tacctggccc tcagcgcagg actggaccgc aggactggtg atctgggccc   2220
tgccacctcc ctggtcctga tctccacatc tccaaggacg agggtgtacc ctctgccacc   2280
cagttgcacc ctttcctgtg ccatctcacc agctctgaac tcaataataa ccttggcatt   2340
gccactgatc tggggctcag gtccttccat gtgcactaat ctcccccccc cacacacac   2400 actgttgctg aaggacaccc caggacccaa catagatcag acaaggctgt gctaggagcc   2460
acaccggtag ggcacctgct ctgggccctg gtagcagtg agtgctgagt ttgtagcctc   2520
aagtgttcaa gtggcacacc aagccaccct cccccagctg tgggcatgct gtgtgccacc   2580
ctgttccagg gatgggagaa gctcctgcca cagccctgta ctgaaaagca gggaagagct   2640
ctgtaggatg ggtgtgtcca gctgggccta gtcaggtgcc ctcactcacg gggttgctcc   2700
tggggcaagg cttgtcttcc tcttcactct gggtgggccc ttggcagctg tggccaccca   2760
tcctaaatag atgagctgct cccctcccac acctgtgcac cttcactggg gtctcaggtc   2820
cagaacagaa gcccatgcac ggctggctta gcaggtctca ggaagggaga ctagagagga   2880
ccttggccta acacagatgc tgcaacaagc ggccctacca tctgtgcaag gctccccaca   2940
agtagccagg cctacctggg cacagggccc cacagcccac atgccaccct aggagtcaag   3000
agccacacag cctcggttta agagcacttt attattgttc ttaaggctac ttttaagtac   3060
g                                                                    3061
```

<210> SEQ ID NO 2
<211> LENGTH: 698
<212> TYPE: PRT
<213> ORGANISM: Mus musculus

<400> SEQUENCE: 2

```
Met Gly Asp Pro Gly Leu Ala Lys Leu Gln Phe Ala Pro Phe Asn Ser
1               5                   10                  15

Ala Leu Asp Val Gly Phe Trp His Glu Leu Thr Gln Lys Lys Leu Asn
            20                  25                  30

Glu Tyr Arg Leu Asp Glu Ala Pro Lys Asp Ile Lys Gly Tyr Tyr Tyr
        35                  40                  45

Asn Gly Asp Ser Ala Gly Leu Pro Thr Arg Leu Thr Leu Glu Phe Ser
    50                  55                  60

Ala Phe Asp Met Ser Ala Ser Thr Pro Ala His Cys Cys Pro Ala Met
65                  70                  75                  80

Gly Thr Leu His Asn Thr Asn Thr Leu Glu Ala Phe Lys Thr Ala Asp
                85                  90                  95

Lys Lys Leu Leu Leu Glu Gln Ser Ala Asn Glu Ile Trp Glu Ala Ile
            100                 105                 110

Lys Ser Gly Ala Ala Leu Glu Asn Pro Met Leu Leu Asn Lys Phe Leu
        115                 120                 125

Leu Leu Thr Phe Ala Asp Leu Lys Lys Tyr His Phe Tyr Tyr Trp Phe
```

-continued

```
            130                 135                 140
Cys Cys Pro Ala Leu Cys Leu Pro Glu Ser Ile Pro Leu Ile Arg Gly
145                 150                 155                 160

Pro Val Ser Leu Asp Gln Arg Leu Ser Pro Lys Gln Ile Gln Ala Leu
                165                 170                 175

Glu His Ala Tyr Asp Asp Leu Cys Arg Ala Glu Gly Val Thr Ala Leu
                180                 185                 190

Pro Tyr Phe Leu Phe Lys Tyr Asp Asp Thr Val Leu Val Ser Leu
                195                 200                 205

Leu Lys His Tyr Ser Asp Phe Phe Gln Gly Gly Arg Thr Lys Ile Thr
    210                 215                 220

Val Gly Val Tyr Asp Pro Cys Asn Leu Ala Gln Tyr Pro Gly Trp Pro
225                 230                 235                 240

Leu Arg Asn Phe Leu Val Leu Ala Ala His Arg Trp Ser Gly Ser Phe
                245                 250                 255

Gln Ser Val Glu Val Leu Cys Phe Arg Asp Arg Thr Met Gln Gly Ala
                260                 265                 270

Arg Asp Val Thr His Ser Ile Ile Phe Glu Val Lys Leu Pro Glu Met
                275                 280                 285

Ala Phe Ser Pro Asp Cys Pro Lys Ala Val Gly Trp Glu Lys Asn Gln
            290                 295                 300

Lys Gly Gly Met Gly Pro Arg Met Val Asn Leu Ser Gly Cys Met Asp
305                 310                 315                 320

Pro Lys Arg Leu Ala Glu Ser Ser Val Asp Leu Asn Leu Lys Leu Met
                325                 330                 335

Cys Trp Arg Leu Val Pro Thr Leu Asp Leu Asp Lys Val Val Ser Val
                340                 345                 350

Lys Cys Leu Leu Leu Gly Ala Gly Thr Leu Gly Cys Asn Val Ala Arg
                355                 360                 365

Thr Leu Met Gly Trp Gly Val Arg His Val Thr Phe Val Asp Asn Ala
    370                 375                 380

Lys Ile Ser Tyr Ser Asn Pro Val Arg Gln Pro Leu Tyr Glu Phe Glu
385                 390                 395                 400

Asp Cys Leu Gly Gly Gly Lys Pro Lys Ala Leu Ala Ala Ala Glu Arg
                405                 410                 415

Leu Gln Lys Ile Phe Pro Gly Val Asn Ala Arg Gly Phe Asn Met Ser
                420                 425                 430

Ile Pro Met Pro Gly His Pro Val Asn Phe Ser Asp Val Thr Met Glu
            435                 440                 445

Gln Ala Arg Arg Asp Val Glu Gln Leu Glu Gln Leu Ile Asp Asn His
    450                 455                 460

Asp Val Ile Phe Leu Leu Met Asp Thr Arg Glu Ser Arg Trp Leu Pro
465                 470                 475                 480

Thr Val Ile Ala Ala Ser Lys Arg Lys Leu Val Ile Asn Ala Ala Leu
                485                 490                 495

Gly Phe Asp Thr Phe Val Val Met Arg His Gly Leu Lys Lys Pro Lys
                500                 505                 510

Gln Gln Gly Ala Gly Asp Leu Cys Pro Ser His Leu Val Ala Pro Ala
                515                 520                 525

Asp Leu Gly Ser Ser Leu Phe Ala Asn Ile Pro Gly Tyr Lys Leu Gly
    530                 535                 540

Cys Tyr Phe Cys Asn Asp Val Val Ala Pro Gly Asp Ser Thr Arg Asp
545                 550                 555                 560
```

```
Arg Thr Leu Asp Gln Gln Cys Thr Val Ser Arg Pro Gly Leu Ala Val
                565                 570                 575

Ile Ala Gly Ala Leu Ala Val Glu Leu Met Val Ser Val Leu Gln His
            580                 585                 590

Pro Glu Gly Gly Tyr Ala Ile Ala Ser Ser Asp Asp Arg Met Asn
        595                 600                 605

Glu Pro Pro Thr Ser Leu Gly Leu Val Pro His Gln Ile Arg Gly Phe
    610                 615                 620

Leu Ser Arg Phe Asp Asn Val Leu Pro Val Ser Leu Ala Phe Asp Lys
625                 630                 635                 640

Cys Thr Ala Cys Ser Pro Lys Val Leu Asp Gln Tyr Glu Arg Glu Gly
                645                 650                 655

Phe Thr Phe Leu Ala Lys Val Phe Asn Ser Ser His Ser Phe Leu Glu
            660                 665                 670

Asp Leu Thr Gly Leu Thr Leu Leu His Gln Glu Thr Gln Ala Ala Glu
        675                 680                 685

Ile Trp Asp Met Ser Asp Glu Glu Thr Val
        690                 695

<210> SEQ ID NO 3
<211> LENGTH: 2032
<212> TYPE: DNA
<213> ORGANISM: Mus musculus

<400> SEQUENCE: 3
gagtcttcag ctagccgacc gggaagtagc tgaagaccgg gcgatgggaa ctctggaggt      60
ctcgctccgg ggcggacccg aggccaccgt gccccgcgg  tagaacgagc tgggtggcg     120 ggctccgggc tcctgaggca tggaggggtc taaggcgtcc agcagcacca tgcaggtgag    180
cttcgtgtgc cagcgctgta gccagcctct gaaactggac acgagcttca agatcctgga    240
ccgggtcacc atccaggaac tcacagctcc attacttacc acagcccagg cgaaaccagg    300
agagacccag gaggaagagg ctaactcagg agaggagcca tttattgaaa ctcgccagga    360
tggtgtctct cgaagattca tcccccccagc caggatgatg tctacagaaa gtgctaatag    420
cttcactctg atcggggagg catctgatgg tggcaccatg gagaacctca gccggagact    480
caaggtcact ggagacctgt tgacatcat gtcgggccag accgatgtgg atcacccgct    540
gtgtgaggaa tgcacagaca ctcttttaga ccagctggac actcagctca atgtcactga    600
gaatgaatgt cagaactaca aacgctgttt ggagatccta gagcagatga atgaggatga    660
cagtgagcag ctgcagaggg agctgaagga gctggccttg gaggaggaga ggctgatcca    720
ggagctggaa gatgtggaaa agaaccgcaa ggtggtggca gagaacctgg agaaggtcca    780
ggctgaggcg agagattgg accaggagga agctcagtac cagcgggagt atagtgagtt    840
taaaaggcag cagctggagt tggatgacga actcaagagt gtggagaacc aggtgcgcta    900
cgcccagatc cagctggaca agctcaagaa aaccaatgtc ttcaatgcca ccttccacat    960
ctggcacagc ggacagtttg cacaatcaa taatttcaga ctgggtcgct tgcccagtgt   1020
tcctgtggag tggaatgaaa tcaatgctgc ctggggccag acagtgctgc tgctccatgc   1080
tttggccaat aagatgggtc tgaagtttca gaggtaccga cttgttccct atggaaatca   1140
ttcctatctg gagtctctga cagacaaatc taaggagttg ccgttatact gttctggggg   1200
tttgcggttt ttctgggaca acaagtttga ccatgcaatg gtagcttttc tggactgtgt   1260
gcagcagttc aaagaagagg tggaaaaagg agagactcga ttttgtcttc cgtacaggat   1320
```

-continued

```
ggacgtggag aaaggcaaga ttgaagacac tggaggcagt ggcggctcct attccatcaa    1380
aacccagttt aactcggagg agcagtggac aaaagcgctc aagttcatgc tgaccaatct    1440
caagtggggt cttgcctggg tgtcctcaca gttctataac aagtgacttg ctccttaggg    1500
gatgtttgcc tttaaggttt tatactttgt ttggtttgga aagatgcttt aaattaaatt    1560
tgggtaatat taaccacat gtttacaata ccaaaatcca caaaagctac tttattttca     1620
aatatgacag atagtttcca gagtacgcca tgtatagcaa agaaccctgc catagttttg    1680
actcagcccc atgcatcctt tccctctttc ctgaaaacaa ctaatttaaa tttgctttgt    1740
tttctttttt aagttgaatt gacgttaatg tgttttcact ggatttttatc tctctcaact   1800 tcctgcactt aaaatttgaa acagcaaagg tttgagatga gatgcttgtg cacacagtt     1860 gggtgatgtg gggaaaggac accgggtcag gagttgcaag tttaactccg tcctcacttg    1920
tagcattgaa tgcctcctgt gctgtctagt gggactacag aatgctgttt gatactgtgt    1980
gcgacgtgga gagatttaat tatttgtaat aaaggatttg ctatggtcta tt            2032
```

<210> SEQ ID NO 4
<211> LENGTH: 448
<212> TYPE: PRT
<213> ORGANISM: Mus musculus

<400> SEQUENCE: 4

```
Met Glu Gly Ser Lys Ala Ser Ser Thr Met Gln Val Ser Phe Val
1               5                   10                  15

Cys Gln Arg Cys Ser Gln Pro Leu Lys Leu Asp Thr Ser Phe Lys Ile
                20                  25                  30

Leu Asp Arg Val Thr Ile Gln Glu Leu Thr Ala Pro Leu Leu Thr Thr
            35                  40                  45

Ala Gln Ala Lys Pro Gly Glu Thr Gln Glu Glu Ala Asn Ser Gly
        50                  55                  60

Glu Glu Pro Phe Ile Glu Thr Arg Gln Asp Gly Val Ser Arg Arg Phe
65                  70                  75                  80

Ile Pro Pro Ala Arg Met Met Ser Thr Glu Ser Ala Asn Ser Phe Thr
                85                  90                  95

Leu Ile Gly Glu Ala Ser Asp Gly Gly Thr Met Glu Asn Leu Ser Arg
            100                 105                 110

Arg Leu Lys Val Thr Gly Asp Leu Phe Asp Ile Met Ser Gly Gln Thr
        115                 120                 125

Asp Val Asp His Pro Leu Cys Glu Glu Cys Thr Asp Thr Leu Leu Asp
    130                 135                 140

Gln Leu Asp Thr Gln Leu Asn Val Thr Glu Asn Glu Cys Gln Asn Tyr
145                 150                 155                 160

Lys Arg Cys Leu Glu Ile Leu Glu Gln Met Asn Glu Asp Asp Ser Glu
                165                 170                 175

Gln Leu Gln Arg Glu Leu Lys Glu Leu Ala Leu Glu Glu Arg Leu
            180                 185                 190

Ile Gln Glu Leu Glu Asp Val Glu Lys Asn Arg Lys Val Val Ala Glu
        195                 200                 205

Asn Leu Glu Lys Val Gln Ala Glu Ala Glu Arg Leu Asp Gln Glu Glu
    210                 215                 220

Ala Gln Tyr Gln Arg Glu Tyr Ser Glu Phe Lys Arg Gln Gln Leu Glu
225                 230                 235                 240

Leu Asp Asp Glu Leu Lys Ser Val Glu Asn Gln Val Arg Tyr Ala Gln
```

-continued

```
            245                 250                 255
Ile Gln Leu Asp Lys Leu Lys Lys Thr Asn Val Phe Asn Ala Thr Phe
            260                 265                 270

His Ile Trp His Ser Gly Gln Phe Gly Thr Ile Asn Asn Phe Arg Leu
            275                 280                 285

Gly Arg Leu Pro Ser Val Pro Val Glu Trp Asn Glu Ile Asn Ala Ala
            290                 295                 300

Trp Gly Gln Thr Val Leu Leu His Ala Leu Ala Asn Lys Met Gly
305                 310                 315                 320

Leu Lys Phe Gln Arg Tyr Arg Leu Val Pro Tyr Gly Asn His Ser Tyr
            325                 330                 335

Leu Glu Ser Leu Thr Asp Lys Ser Lys Glu Leu Pro Leu Tyr Cys Ser
            340                 345                 350

Gly Gly Leu Arg Phe Phe Trp Asp Asn Lys Phe Asp His Ala Met Val
            355                 360                 365

Ala Phe Leu Asp Cys Val Gln Gln Phe Lys Glu Val Glu Lys Gly
            370                 375                 380

Glu Thr Arg Phe Cys Leu Pro Tyr Arg Met Asp Val Glu Lys Gly Lys
385                 390                 395                 400

Ile Glu Asp Thr Gly Gly Ser Gly Ser Tyr Ser Ile Lys Thr Gln
            405                 410                 415

Phe Asn Ser Glu Glu Gln Trp Thr Lys Ala Leu Lys Phe Met Leu Thr
            420                 425                 430

Asn Leu Lys Trp Gly Leu Ala Trp Val Ser Ser Gln Phe Tyr Asn Lys
            435                 440                 445

<210> SEQ ID NO 5
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 5
cagtttggca caatcaata                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
gtttgtagcc tcaagtgtt                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic Construct

<400> SEQUENCE: 7
ccactagtct gactgatga                                                19

<210> SEQ ID NO 8
<211> LENGTH: 19
<212> TYPE: DNA
<213> ORGANISM: Artificial Sequence
```

```
<220> FEATURE:
<223> OTHER INFORMATION: Synthetic Construct

<400> SEQUENCE: 8
tgagatactc gaggtggat                                                    19

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct

<400> SEQUENCE: 9
cattcgatct cattcagta                                                    19

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
gatcgaggat tatgaaaga                                                    19

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
caaggagtgg tgttgttaa                                                    19

<210> SEQ ID NO 12
<211> LENGTH: 19
<212> TYPE: DNA
<213> ORGANISM: Artificial Sequence
<220> FEATURE:
<223> OTHER INFORMATION: Synthetic Construct

<400> SEQUENCE: 12
cttgtctctg ctcttatga                                                    19

<210> SEQ ID NO 13
<211> LENGTH: 19
<212> TYPE: DNA
<213> ORGANISM: Artificial Sequence
<220> FEATURE:
<223> OTHER INFORMATION: Synthetic Construct

<400> SEQUENCE: 13
ttagcaagat ttggcgata                                                    19

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
gacgttgact ggcttgttc                                                    19
```

<210> SEQ ID NO 15
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15
tgacacgcta tttctacct                                               19

<210> SEQ ID NO 16
<211> LENGTH: 19
<212> TYPE: DNA
<213> ORGANISM: Artificial Sequence
<220> FEATURE:
<223> OTHER INFORMATION: Synthetic Construct

<400> SEQUENCE: 16
cagtttggca caatcaata                                               19

<210> SEQ ID NO 17
<211> LENGTH: 19
<212> TYPE: DNA
<213> ORGANISM: Artificial Sequence
<220> FEATURE:
<223> OTHER INFORMATION: Synthetic Construct

<400> SEQUENCE: 17
ggagtcacag ctcttcctt                                               19

<210> SEQ ID NO 18
<211> LENGTH: 2396
<212> TYPE: DNA
<213> ORGANISM: Homo sapiens

<400> SEQUENCE: 18
ggaagttgag cggcggcaag aaataatggc ggcagctacg ggggatcctg gactctctaa     60
actgcagttt gccccttta gtagtgcctt ggatgttggg ttttggcatg agttgaccca     120
gaagaagctg aacgagtatc ggctggatga agctcccaag gacattaagg gttattacta    180
caatggtgac tctgctgggc tgccagctcg cttaacattg gagttcagtg cttttgacat    240
gagtgctccc accccagccc gttgctgccc agctattgga acactgtata acaccaacac    300
actcgagtct ttcaagactg cagataagaa gctcctttg gaacaagcag caaatgagat    360
atgggaatcc ataaaatcag gcactgctct tgaaaaccct gtactcctca acaagttcct    420
cctcttgaca tttgcagatc taagaagta ccacttctac tattggtttt gctatcctgc    480
cctctgtctt ccagagagtt tacctctcat tcagggggcca gtgggtttgg atcaaaggtt    540
ttcactaaaa cagattgaag cactagagtg tgcatatgat aatctttgtc aaacagaagg    600
agtcacagct cttccttact tcttaatcaa gtatgatgag aacatggtgc tggtttcctt    660
gcttaaacac tacagtgatt tcttccaagg tcaaaggacg aagataacaa ttggtgtata    720
tgatccctgt aacttagccc agtacccctgg atggcctttg aggaattttt tggtcctagc    780
agcccacaga tggagtagca gtttccagtc tgttgaagtt gtttgcttcc gtgaccgtac    840
catgcagggg gcgagagacg ttgcccacag catcatcttc gaagtgaagc ttccagaaat    900
ggcatttagc ccagattgtc ctaaagcagt tggatgggaa agaaccagaa aggaggcat    960 gggaccaagg atggtgaacc tcagtgaatg tatggaccct aaaaggttag ctgagtcatc    1020
agtggatcta aatctcaaac tgatgtgttg gagattggtt cctactttag acttggacaa    1080

```
ggttgtgtct gtcaaatgtc tgctgcttgg agccggcacc ttgggttgca atgtagctag   1140
gacgttgatg ggttggggcg tgagacacat cacatttgtg gacaatgcca agatctccta   1200
ctccaatcct gtgaggcagc ctctctatga gtttgaagat tgcctagggg gtggtaagcc   1260
caaggctctg gcagcagcgg accggctcca gaaaatattc cccggtgtga atgccagagg   1320
attcaacatg agcatatccta tgcctgggca tccagtgaac ttctccagtg tcactctgga   1380
gcaagcccgc agagatgtgg agcaactgga gcagctcatc gaaagccatg atgtcgtctt   1440
cctattgatg gacaccaggg agagccggtg gcttcctgcc gtcattgctg caagcaagag   1500
aaagctggtc atcaatgctg ctttgggatt tgacacattt gttgtcatga gacatggtct   1560
gaagaaacca agcagcaag gagctgggga cttgtgtcca aaccaccctg tggcatctgc   1620
tgacctcctg ggctcatcgc tttttgccaa catccctggt tacaagcttg gctgctactt   1680
ctgcaatgat gtggtggccc caggagattc aaccagagac cggaccttgg accagcagtg   1740
cactgtgagt cgtccaggac tggccgtgat tgcaggagcc ctggccgtgg aattgatggt   1800
atctgttttg cagcatccag aaggggggcta tgccattgcc agcagcagtg acgatcggat   1860
gaatgagcct ccaacctctc ttgggcttgt gcctcaccag atccggggat ttctttcacg   1920
gtttgataat gtccttcccg tcagcctggc atttgacaaa tgtacagctt gttcttccaa   1980
agttcttgat caatatgaac gagaaggatt taacttccta gccaaggtgt ttaattcttc   2040
acattccttc ttagaagact tgactggtct tacattgctg catcaagaaa cccaagctgc   2100
tgagatctgg gacatgagcg atgatgagac catctgagat ggccccgctg tggggctgac   2160 ttctcccctgg ccgcctgctg aggagctctc catcgccaga gcaggactgc tgaccccagg   2220
cctggtgatt ctgggcccct cctccatacc ccgaggtctg ggattccccc ctctgctgcc   2280
caggagtggc cagtgttcgg cgttgctcgg gattcaagat accaccagtt cagagctaaa   2340
taataacctt ggccttggcc ttgctattga cctgggaaaa aaaaaaaaaa aaaaaa        2396
```

<210> SEQ ID NO 19
<211> LENGTH: 703
<212> TYPE: PRT
<213> ORGANISM: Homo sapiens

<400> SEQUENCE: 19

```
Met Ala Ala Ala Thr Gly Asp Pro Gly Leu Ser Lys Leu Gln Phe Ala
1               5                   10                  15

Pro Phe Ser Ser Ala Leu Asp Val Gly Phe Trp His Glu Leu Thr Gln
            20                  25                  30

Lys Lys Leu Asn Glu Tyr Arg Leu Asp Glu Ala Pro Lys Asp Ile Lys
        35                  40                  45

Gly Tyr Tyr Tyr Asn Gly Asp Ser Ala Gly Leu Pro Ala Arg Leu Thr
    50                  55                  60

Leu Glu Phe Ser Ala Phe Asp Met Ser Ala Pro Thr Pro Ala Arg Cys
65                  70                  75                  80

Cys Pro Ala Ile Gly Thr Leu Tyr Asn Thr Asn Thr Leu Glu Ser Phe
                85                  90                  95

Lys Thr Ala Asp Lys Lys Leu Leu Glu Gln Ala Ala Asn Glu Ile
            100                 105                 110

Trp Glu Ser Ile Lys Ser Gly Thr Ala Leu Glu Asn Pro Val Leu Leu
        115                 120                 125

Asn Lys Phe Leu Leu Leu Thr Phe Ala Asp Leu Lys Lys Tyr His Phe
    130                 135                 140
```

-continued

```
Tyr Tyr Trp Phe Cys Tyr Pro Ala Leu Cys Leu Pro Glu Ser Leu Pro
145                 150                 155                 160

Leu Ile Gln Gly Pro Val Gly Leu Asp Gln Arg Phe Ser Leu Lys Gln
                165                 170                 175

Ile Glu Ala Leu Glu Cys Ala Tyr Asp Asn Leu Cys Gln Thr Glu Gly
            180                 185                 190

Val Thr Ala Leu Pro Tyr Phe Leu Ile Lys Tyr Asp Glu Asn Met Val
            195                 200                 205

Leu Val Ser Leu Leu Lys His Tyr Ser Asp Phe Phe Gln Gly Gln Arg
210                 215                 220

Thr Lys Ile Thr Ile Gly Val Tyr Asp Pro Cys Asn Leu Ala Gln Tyr
225                 230                 235                 240

Pro Gly Trp Pro Leu Arg Asn Phe Leu Val Leu Ala Ala His Arg Trp
                245                 250                 255

Ser Ser Ser Phe Gln Ser Val Glu Val Val Cys Phe Arg Asp Arg Thr
                260                 265                 270

Met Gln Gly Ala Arg Asp Val Ala His Ser Ile Ile Phe Glu Val Lys
            275                 280                 285

Leu Pro Glu Met Ala Phe Ser Pro Asp Cys Pro Lys Ala Val Gly Trp
290                 295                 300

Glu Lys Asn Gln Lys Gly Gly Met Gly Pro Arg Met Val Asn Leu Ser
305                 310                 315                 320

Glu Cys Met Asp Pro Lys Arg Leu Ala Glu Ser Ser Val Asp Leu Asn
                325                 330                 335

Leu Lys Leu Met Cys Trp Arg Leu Val Pro Thr Leu Asp Leu Asp Lys
            340                 345                 350

Val Val Ser Val Lys Cys Leu Leu Leu Gly Ala Gly Thr Leu Gly Cys
            355                 360                 365

Asn Val Ala Arg Thr Leu Met Gly Trp Gly Val Arg His Ile Thr Phe
370                 375                 380

Val Asp Asn Ala Lys Ile Ser Tyr Ser Asn Pro Val Arg Gln Pro Leu
385                 390                 395                 400

Tyr Glu Phe Glu Asp Cys Leu Gly Gly Gly Lys Pro Lys Ala Leu Ala
                405                 410                 415

Ala Ala Asp Arg Leu Gln Lys Ile Phe Pro Gly Val Asn Ala Arg Gly
            420                 425                 430

Phe Asn Met Ser Ile Pro Met Pro Gly His Pro Val Asn Phe Ser Ser
            435                 440                 445

Val Thr Leu Glu Gln Ala Arg Arg Asp Val Glu Gln Leu Glu Gln Leu
450                 455                 460

Ile Glu Ser His Asp Val Val Phe Leu Leu Met Asp Thr Arg Glu Ser
465                 470                 475                 480

Arg Trp Leu Pro Ala Val Ile Ala Ser Lys Arg Lys Leu Val Ile
                485                 490                 495

Asn Ala Ala Leu Gly Phe Asp Thr Phe Val Val Met Arg His Gly Leu
            500                 505                 510

Lys Lys Pro Lys Gln Gln Gly Ala Gly Asp Leu Cys Pro Asn His Pro
            515                 520                 525

Val Ala Ser Ala Asp Leu Leu Gly Ser Ser Leu Phe Ala Asn Ile Pro
            530                 535                 540

Gly Tyr Lys Leu Gly Cys Tyr Phe Cys Asn Asp Val Val Ala Pro Gly
545                 550                 555                 560
```

```
Asp Ser Thr Arg Asp Arg Thr Leu Asp Gln Gln Cys Thr Val Ser Arg
            565                 570                 575

Pro Gly Leu Ala Val Ile Ala Gly Ala Leu Ala Val Glu Leu Met Val
        580                 585                 590

Ser Val Leu Gln His Pro Glu Gly Gly Tyr Ala Ile Ala Ser Ser Ser
    595                 600                 605

Asp Asp Arg Met Asn Glu Pro Pro Thr Ser Leu Gly Leu Val Pro His
    610                 615                 620

Gln Ile Arg Gly Phe Leu Ser Arg Phe Asp Asn Val Leu Pro Val Ser
625                 630                 635                 640

Leu Ala Phe Asp Lys Cys Thr Ala Cys Ser Lys Val Leu Asp Gln
                645                 650                 655

Tyr Glu Arg Glu Gly Phe Asn Phe Leu Ala Lys Val Phe Asn Ser Ser
            660                 665                 670

His Ser Phe Leu Glu Asp Leu Thr Gly Leu Thr Leu Leu His Gln Glu
        675                 680                 685

Thr Gln Ala Ala Glu Ile Trp Asp Met Ser Asp Asp Glu Thr Ile
    690                 695                 700

<210> SEQ ID NO 20
<211> LENGTH: 2144
<212> TYPE: DNA
<213> ORGANISM: Homo sapiens

<400> SEQUENCE: 20
gctgaagaca gagcgatggt agttctggag gcctcgctcc ggggccgacc cgaggccaca        60
gtgcctccgc ggtagaccgg acttgggtga cgggctccgg gctcccgagg tgaagagcat       120
cgggggctga gggatggaag ggtctaagac gtccaacaac agcaccatgc aggtgagctt       180
cgtgtgccag cgctgcagcc agcccctgaa actggacacg agtttcaaga tcctggaccg       240
tgtcaccatc caggaactca cagctccatt acttaccaca gcccaggcga aaccaggaga       300
gacccaggag gaagagacta actcaggaga ggagccattt attgaaactc ctcgccagga       360
tggtgtctct cgcagattca tccccccagc caggatgatg tccacagaaa gtgccaacag       420
cttcactctg attggggagg catctgatgg cggcaccatg gagaacctca gccgaagact       480
gaaggtcact gggaccttt ttgacatcat gtcgggccag acagatgtgg atcccccact       540
ctgtgaggaa tgcacagata ctcttttaga ccagctggac actcagctca acgtcactga       600
aaatgagtgt cagaactaca aacgctgttt ggagatctta gagcaaatga atgaggatga       660
cagtgaacag ttacagatgg agctaaagga gctggcacta gaggaggaga ggctgatcca       720
ggagctggaa gacgtggaaa agaaccgcaa gatagtggca gaaaatctcg agaaggtcca       780
ggctgaggct gagagactgg atcaggagga agctcagtat cagagagaat acagtgaatt       840
taaacgacag cagctggagc tggatgatga gctgaagagt gttgaaaacc agatgcgtta       900
tgcccagacg cagctggata agctgaagaa aaccaacgtc tttaatgcaa ccttccacat       960
ctggcacagt ggacagtttg cacaatcaa taacttcagg ctgggtcgcc tgcccagtgt      1020
tcccgtggaa tggaatgaga ttaatgctgc ttggggccag actgtgttgc tgctccatgc      1080
tctggccaat aagatgggtc tgaaatttca gagataccga cttgttcctt acggaaacca      1140
ttcatatctg gagtctctga cagacaaatc taaggagctg ccgttatact gttctggggg      1200
gttgcggttt ttctgtggga caacaagttga ccatgcaatg gtggcttcc tggactgtgt      1260 gcagcagttc aaagaagagg ttgagaaagg cgagacacgt ttttgtcttc cctacaggat      1320
```

-continued

```
ggatgtggag aaaggcaaga ttgaagacac aggaggcagt ggcggctcct attccatcaa   1380
aacccagttt aactctgagg agcagtggac aaaagctctc aagttcatgc tgacgaatct   1440
taagtggggt cttgcttggg tgtcctcaca attttataac aaatgacttt tttccttagg   1500
gggaggtttg ccttaaaggc ttttaatttt gttttgtttg caaacatgtt ttaaattaaa   1560
ttcgggtaat attaaacagt acatgtttac aataccaaaa aagaaaaaat ccacaaaagc   1620
cactttattt taaatatca tgtgacagat actttccaga gctacaacat gccatctata   1680
gttgccagcc ctggtcagtt ttgattctta accccatgga ctcctttccc tttcttctct   1740 gaaaaaact aatttaaatt tgcttttctt tttttaact gagttgaatt gagattgatg   1800
tgttttcact ggatttttat ctctctcaac ttcctgcact taacaatatg aaatagaaac   1860
ttttgtcttt actgagatga ggatatgttt gagatgcaca gttggataat gtgggaaaat   1920
gacatctaag ctttacctgg tcaccatgtg atgtgatcag atgcttgaaa tttaacactt   1980
ttcacttggt tcttatactg aatgccgact ctgctctgtg ttagagatat gaaatggtgt   2040
ttgatactgt ttgagacatt atggagagat ttaattattt gtaataaaag atttgctgca   2100
gtctgaaaac tgaaaaaaaa aaaaaaaaaa aaaaaaaaaa aaaa               2144
```

<210> SEQ ID NO 21
<211> LENGTH: 450
<212> TYPE: PRT
<213> ORGANISM: Homo sapiens

<400> SEQUENCE: 21

```
Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys
            20                  25                  30

Ile Leu Asp Arg Val Thr Ile Gln Glu Leu Thr Ala Pro Leu Leu Thr
        35                  40                  45

Thr Ala Gln Ala Lys Pro Gly Glu Thr Gln Glu Glu Thr Asn Ser
    50                  55                  60

Gly Glu Glu Pro Phe Ile Glu Thr Pro Arg Gln Asp Gly Val Ser Arg
65                  70                  75                  80

Arg Phe Ile Pro Pro Ala Arg Met Met Ser Thr Glu Ser Ala Asn Ser
                85                  90                  95

Phe Thr Leu Ile Gly Glu Ala Ser Asp Gly Gly Thr Met Glu Asn Leu
            100                 105                 110

Ser Arg Arg Leu Lys Val Thr Gly Asp Leu Phe Asp Ile Met Ser Gly
        115                 120                 125

Gln Thr Asp Val Asp His Pro Leu Cys Glu Glu Cys Thr Asp Thr Leu
    130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu
            180                 185                 190

Arg Leu Ile Gln Glu Leu Glu Asp Val Glu Lys Asn Arg Lys Ile Val
        195                 200                 205

Ala Glu Asn Leu Glu Lys Val Gln Ala Glu Ala Glu Arg Leu Asp Gln
    210                 215                 220

Glu Glu Ala Gln Tyr Gln Arg Glu Tyr Ser Glu Phe Lys Arg Gln Gln
```

-continued

```
            225                 230                 235                 240

Leu Glu Leu Asp Asp Glu Leu Lys Ser Val Glu Asn Gln Met Arg Tyr
                245                 250                 255

Ala Gln Thr Gln Leu Asp Lys Leu Lys Lys Thr Asn Val Phe Asn Ala
                260                 265                 270

Thr Phe His Ile Trp His Ser Gly Gln Phe Gly Thr Ile Asn Asn Phe
            275                 280                 285

Arg Leu Gly Arg Leu Pro Ser Val Pro Val Glu Trp Asn Glu Ile Asn
        290                 295                 300

Ala Ala Trp Gly Gln Thr Val Leu Leu Leu His Ala Leu Ala Asn Lys
305                 310                 315                 320

Met Gly Leu Lys Phe Gln Arg Tyr Arg Leu Val Pro Tyr Gly Asn His
                325                 330                 335

Ser Tyr Leu Glu Ser Leu Thr Asp Lys Ser Lys Glu Leu Pro Leu Tyr
                340                 345                 350

Cys Ser Gly Gly Leu Arg Phe Phe Trp Asp Asn Lys Phe Asp His Ala
                355                 360                 365

Met Val Ala Phe Leu Asp Cys Val Gln Gln Phe Lys Glu Glu Val Glu
            370                 375                 380

Lys Gly Glu Thr Arg Phe Cys Leu Pro Tyr Arg Met Asp Val Glu Lys
385                 390                 395                 400

Gly Lys Ile Glu Asp Thr Gly Gly Ser Gly Ser Tyr Ser Ile Lys
                405                 410                 415

Thr Gln Phe Asn Ser Glu Glu Gln Trp Thr Lys Ala Leu Lys Phe Met
                420                 425                 430

Leu Thr Asn Leu Lys Trp Gly Leu Ala Trp Val Ser Ser Gln Phe Tyr
            435                 440                 445

Asn Lys
    450
```

FUNCTION OF AUTOPHAGY GENES IN CELL DEATH

CROSS REFERENCE TO RELATED APPLICATIONS

This application claims the benefit from U.S. Provisional Application Ser. No. 60/566,857, filed Apr. 30, 2004, the content of which is hereby incorporated by reference herein for all purposes.

GOVERNMENTAL INTERESTS

This invention was made with governmental support under Grant No. GM59136, awarded by The National Institutes of Health. The government has certain rights in the invention.

BACKGROUND OF THE INVENTION

1. Field of the Invention

The present invention relates generally to cell death, and more particularly, to methods and compositions for regulating cell death through activating the autophagic pathway.

2. Background of the Related Art

Apoptosis is a well-studied pathway of programmed cell death conserved from C. elegans to humans (1). Caspases, a family of cystinyl, aspartate-requiring proteases produce the morphological changes associated with apoptotic death (2, 3). Non-apoptotic forms of cell elimination include those with features of necrosis and autophagy (4-7). Autophagy is a process that liberates free amino acids and nucleotides and enables cells to survive under nutrient deprivation conditions as well as to undergo structural remodeling during differentiation. Necrosis can result when cell metabolism and integrity are compromised by a nonphysiological insult.

During autophagy, isolation membranes are used to sequester cytoplasmic components, such as proteins and organelles including mitochondria, and target these membrane-bound structures for degradation by fusion with lysosomes (8, 29). Genetic studies of autophagy induced by nutrient starvation in the yeast *Saccharomyces cerevisiae* resulted in the identification of the ATG genes (30-33). ATG genes are involved in the activation of the signaling complex that triggers formation of autophagic structures from isolation membranes that are known as autophagosomes, and this process involves two ubiquitination-like pathways (8). Autophagosomes then dock and fuse with lysosomes where they are degraded.

Autophagy has been observed in various eukaryotic organisms, and the ATG genes appear to be conserved in organisms, that are as different as yeast and humans (10). The ATG genes appear to be a survival response to nutritional starvation involving membrane-bound vacuoles that target organelles and proteins to the lysosome for degradation (8, 9).

Morphological studies of dying cells during embryogenesis resulted in the identification of at least two prominent forms of physiological cell death (34, 35). These dying cells were distinguished based on how they are degraded and removed dying cells. Cells undergoing autophagy digest themselves by formation of autophagosomes that transport degraded cargo to the lysosome. In contrast, during apoptosis, phagocytes eat dying cells and the dead cells are degraded by the lysosome of the phagocyte. Apoptosis has been a subject of intense investigation in recent years and two general mechanisms has been described for inducing this type of cell death (1). The intrinsic apoptosis pathway relies on the mitochondria for regulatory components that are involved in the activation of caspase proteases that cleave death-inducing protein substrates. The extrinsic apoptosis pathway depends on extracellular death ligands such as TNF and Fas, and these ligands are bound by trimeric death receptors that recruit adapter proteins, such as FADD and TRADD, that recruit caspases 8 and 10. The proximity of these caspases within signaling complexes results in their proteolytic activation and cell death.

Several groups have observed necrosis-like cell death that appears to occur in a caspase independent manner (16). Furthermore, non-apoptotic cell death appears to provide a compensatory mechanism for cell killing when apoptotic regulators such as caspases and Apaf1 are compromised (36, 37). Thus, it would be beneficial to determine methods, enzymatic pathways and compounds that induce such non-apoptotic mechanisms to compensate when programmed death by apoptosis is compromised.

SUMMARY OF THE INVENTION

The present invention relates to composition and methods for regulating cell death by inducing the autophagic pathway.

In one aspect, the present invention relates to a composition for inducing autophagic cell death, the composition comprising a Caspase 8 inhibitor and at least one protein expressed by an ATG gene or variant thereof. Preferably, the ATG gene includes Atg 7 and beclin or mammalian homologs thereof. Atg 7 is a key autophagy gene encoding a protein resembling E ubiquitin-activating enzyme that is used in both of the ubiquitin-like pathways required for autophagic vacuoles in yeast (16, 17). Beclin encodes a Bcl-2 interacting candidate tumor suppressor and antiviral protein (18, 19).

In another aspect, the present invention relates to a nucleotide sequence comprising at least two ATG genes selected from APG6, Beclin 1, Atg 7, HsGSA7 and human homologs thereof for inclusion in an expression vector for transfection in cells.

In another aspect, the present invention relates to a method for inducing autophagic cell death in a mammalian cancer cell line, the method comprising administering a caspase-8 inhibitor to the cell either alone or in combination with at least one nucleotide sequence for ATG genes selected from APG6, Beclin 1, Atg 7, HsGSA7 and human homologs thereof.

In still another aspect, the present invention relates to a method for inhibiting cell death in a mammalian cell, the method comprising reducing expression of receptor interacting protein (RIP) and inhibiting caspase 8 in the mammalian cell.

Another aspect of the present invention relates to a method for inducing and increasing autophagic cell death in mammalian cells, the method comprising reducing expression of caspase 8 and increasing expression of ATG7 (HsGSA7/mAPG7) or Beclin 1.

Yet, another aspect of the present invention relates to a method for increasing cell death by the autophagy pathway, the method comprising increasing expression of ATG7 (HsGSA7/mAPG7) or Beclin 1 or human homologs thereof.

A further aspect of the present invention relates to a method of treating a viral infection caused by a virus expressing a caspase 8 inhibitor, the method comprising administering an effective amount of a composition comprising ATG genes including mammalian Beclin and/or Atg7. Preferably, both ATG genes are included in an expression vector.

Another aspect of the present invention relates to a method of inducing the autophagic pathway, the method comprising increasing expression of receptor interacting protein (RIP) and/or Jun N-terminal kinase (JNK) and inhibiting cleavage of RIP.

Still another aspect of the present invention relates to a method for determining compounds that induce the autophagy pathway; the method comprising:
- introducing a caspase 8 inhibitor to a cell;
- introducing an ATG7 and/or beclin gene inhibitor to the cell;
- contacting the cell with a testing compound and determining levels of vacuoles relative to vacuoles before introduction of testing compounds, wherein an increased level of vacuoles indicates a compound that induces the autophagic pathway.

Other features and advantages of the invention will be apparent from the following detailed description, figures and claims.

DETAILED DESCRIPTION OF THE INVENTION

1. Invention

Figure 1A:
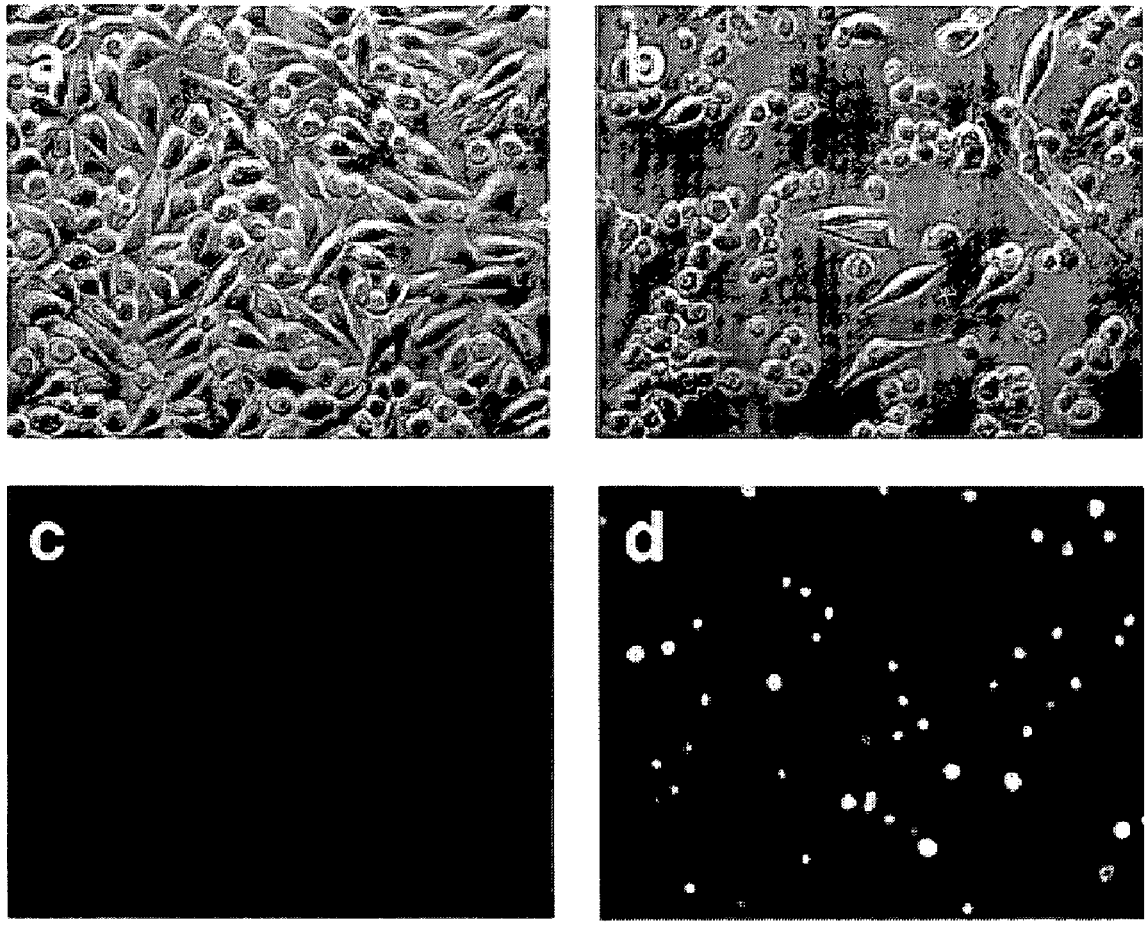
FIGS. 1 A-H show the autophagy results when using a Caspase 8 inhibitor zVAD in combination with different ATG genes.

Autophagy is used to degrade components of the cytoplasm and functions as a cell survivor mechanism during nutrient deprivation. Autophagic structures have also been observed in many type of dying cells but heretofore experimental evidence for autophagy playing a role in the regulation of programmed cell death was limited. Results set forth herein show that the autography genes Atg7 and Beclin 1 are required for the death of certain cells when induced by caspase-8 inhibition. Further, a new molecular pathway was discovered in which activation of the receptor interacting protein (RIP) and Jun N-terminal kinase (JNK) induced cell death with the morphology of autophagy. Additionally, the results set forth herein indicate that signaling through the serine-threonine kinase RIP is essential for autophagic cell death. Further, it was observed that RIP is cleaved and inactivated by caspase 8 providing a mechanism for the prevention of autophagic cell death. Thus, inhibition of caspase 8 allows RIP to transmit the signal needed to kill the cell through the autophagic pathway.

2. Definitions

In order to facilitate review of the various embodiments of the invention and provide an understanding of the various elements and constituents used in making and using the present invention, the following terms used in the invention description have the following meanings.

A "gene," as used herein means a nucleic acid molecule, the sequence of which includes all the information required for the normal regulated production of a particular protein, including the structural coding sequence, promoters and enhancers.

"Amino acid sequence," as used herein, refers to an oligopeptide, peptide, polypeptide, or protein sequence, and fragment thereof, and to naturally occurring or synthetic molecules. Fragments of a polypeptide comprise amino acid sequences that retain the biological activity or the immunological activity of the full polypeptide.

The term "caspase-8 inhibitor," as used herein refers to any compound, molecule or agent that inhibitors the apoptosis activity of caspase-8. The caspase-8 inhibitor may include but is not limited to: antibodies that form a complex with caspase 8, benzyloxycarbonyl-valyl-alanyl-aspartic acid (O-methyl)-fluoro-methylketone (zVAD), small interfering RNAs for silencing the gene that express caspase 8, Z-IETD-FMK, etc.

The term "biologically active," as used herein, refers to a protein having structural, regulatory, or biochemical functions of a naturally occurring molecule. The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands.

The term "homology," as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

"Nucleic acid sequence," as used herein refers to an oligonucleotide, nucleotide, or polynucleotide, and to DNA or RNA of genomic or synthetic origin that may be single- or double-stranded, and represent the sense or antisense strand.

The term "stringent conditions," as used herein, refers to conditions that permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

The term "purified," as used herein, refers to nucleic or amino acid sequences that are removed from their natural environment, isolated or separated, and are at least 60% free, preferably 75% free, and most preferably 90% free from other components with which they are naturally associated.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

A "variant," of a polypeptide, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "homolog," as used herein, refers to a gene or peptide that has essentially the same nucleotide sequence or amino acid residues, respectively and functions as that of the referenced gene or peptide.

3. Polynucleotide

A. Isolated and Purified Polynucleotides

In one aspect, the present invention provides for an isolated and purified polynucleotide sequence comprising at least one ATG gene and preferably, Atg 7, Atg6 or mammalian homologue such as ATG7 (HsGSA7/mAPG7) or Beclin 1.

As used herein, the term "polynucleotide" means a sequence of nucleotides connected by phosphodiester linkages. Polynucleotides are presented herein in the direction from the 5' to the 3' direction. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

The invention comprises a polynucleotide sequence, complementary sequence or variant thereof for ATG genes, preferably ATG7 and Beclin-1 selected from SEQ ID NO: 1 (mouse ATG7), SEQ ID NO: 3 (mouse Beclin), SEQ ID NO: 18 (human ATG7) or SEQ ID NO: 20 (human Beclin) encoding a polypeptide or variant thereof that resembles E ubiquitin-activating enzyme used in both of the ubiquitin-like pathways required for autophagic vacuoles in yeast or a Bcl-2 interacting protein, including SEQ ID NO: 2 (mouse ATG7), or SEQ ID NO: 4 (mouse Beclin), SEQ ID NO: 19 (human ATG7) or SEQ ID NO: 21 (human beclin-1). In particular, a variant polynucleotide sequence will have at least about 80%, more preferably at least about 90%, and most preferably at least about 95% identity to polynucleotide sequence. The polynucleotide is preparable by a process comprising the steps of constructing a library of cDNA clones from a cell that expresses the polypeptide; screening the library with a labeled cDNA probe prepared from RNA that encodes the polypeptide; and selecting a clone that hybridizes to the probe.

B. Probes and Primers

In another aspect, DNA sequence information provided by the present invention allows for the preparation of relatively short DNA (or RNA) sequence having the ability to specifically hybridize to gene sequences of the selected polynucleotide disclosed herein. In these aspects, nucleic acid probes of an appropriate length are prepared based on a consideration of a selected nucleotide sequence. Most importantly, the primers can be used as short interfering RNAs for gene silencing.

Accordingly, a polynucleotide probe or primer molecule of the invention can be used for its ability to selectively form duplex molecules with a gene or complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02M-0.5M NaCl at temperatures of 50° C. to 70° C. Those conditions are particularly selective, and tolerate little, if any, mismatch between the probe and the template or target strand.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

C. Peptides and Gene Transcription Regulatory Peptide

In one embodiment, the present invention contemplates an isolated and purified peptide that modulates programmed cell death. Preferably, the peptide that modulates programmed cell death has at least 60% homology to a peptide comprising an amino acid sequence of SEQ ID NO: 2, SEQ ID NO: 4, SEQ ID NO: 19 and/or SEQ ID NO: 21.

The invention also encompasses peptide variants. A preferred variant is one which has at least about 80%, more preferably at least about 90%, and most preferably at least about 95% amino acid sequence identity to the amino acid sequence selected from the group consisting of SEQ ID NO: 2, SEQ ID NO: 4, SEQ ID NO: 19 and/or SEQ ID NO: 21, and which modulates programmed cell death.

Polypeptides are disclosed herein as amino acid residue sequences. Those sequences are written left to right in the direction from the amino to the carboxyl terminus. In accordance with standard nomenclature, amino acid residue sequences are denominated by either a single letter or a three letter code as indicated below.

| Amino Acid Residue | 3-Letter Code | 1-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like peptide characteristics that modulate programmed cell death. For example, certain amino acids can be substituted for other amino acids in a sequence without appreciable loss of peptide activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

As outlined above, amino acid substitutions are generally therefore based on the relative similarity of the amino acid side-chain substituents, for example, their hydrophobicity, hydrophilicity, charge, size, and the like. Exemplary substitutions which take in consideration various of the foregoing characteristics are well known to those of skill in the art and include: arginine and lysine; glutamate and aspartate; serine and threonine; glutamine and asparagine; and valine, leucine and isoleucine as shown below. The present invention thus contemplates functional or biological equivalents of a peptide as set forth above.

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp; Phe |
| Val | Ile; Leu |

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells.

D. Expression Vectors

In another embodiment, the present invention provides expression vectors comprising polynucleotides sequences that encode for modulating peptides of autophagic cell death. Preferably, expression vectors of the present invention comprise polynucleotides that encode for peptides resembling E ubiquitin-activating enzyme that are used in both of the ubiquitin-like pathways required for autophagic vacuoles in yeast; and/or a Bcl-2 interacting protein, such as SEQ ID NO: 2 (mouse Atg7), SEQ ID NO: 4 (Beclin mouse), SEQ ID NO: 19 (human) and/or SEQ ID NO: 21. Alternatively, such vectors or fragments can code larger polypeptides or peptides which nevertheless include the basic coding region. In any event, it should be appreciated that due to codon redundancy as well as biological functional equivalence, this aspect of the invention is not limited to the particular DNA molecules corresponding to the polypeptide sequences noted above.

The expression vectors of the present invention preferably comprise polynucleotides operatively linked to an enhancer-promoter. More preferably still, expression vectors of the invention comprise a polynucleotide operatively linked to a prokaryotic or eukaryotic promoter.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promote" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized. A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well known in the art. A preferred transcription-terminating region is derived from a bovine growth hormone gene.

Exemplary vectors include the mammalian expression vectors of the pCMV family including pCMV6b and pCMV6c (Chiron Corp., Emeryville Calif.) and pRc/CMV (Invitrogen, San Diego, Calif.). In certain cases, and specifically in the case of these individual mammalian expression vectors, the resulting constructs can require co-transfection with a vector containing a selectable marker such as pSV2neo.

Where expression of recombinant polypeptide of the present invention is desired and a eukaryotic host is contemplated, it is most desirable to employ a vector, such as a plasmid, that incorporates a eukaryotic origin of replication. Additionally, for the purposes of expression in eukaryotic systems, one desires to position the desired peptide encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit, an appropriate polyadenylation site.

The pRc/CMV vector (available from Invitrogen) is an exemplary vector for expressing a polypeptide in mammalian cells, particularly COS, CHO, human MCF-F, human 293T and BHK bovine cells. A polypeptide of the present invention under the control of a CMV promoter can be efficiently expressed in mammalian cells. The pCMV plasmids are a series of mammalian expression vectors of particular utility in the present invention. The vectors are designed for use in essentially all cultured cells and have been successfully expressed in simian COS cells, mouse L cells, CHO cells, and HeLa cells.

E. Transfected Cells

In yet another embodiment, the present invention provides recombinant host cells transformed or transfected with a polynucleotide including the ATG genes discussed herein. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection.

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA or RNA within liposomes, followed by fusion of the liposomes with the cell membrane. The mechanism of how nucleotides are delivered into the cell is unclear but transfection efficiencies can be as high as 90%.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

F. Preparation of Polypeptides

In yet another embodiment, the present invention contemplates a process of preparing peptides comprising transfecting cells with a polynucleotide that encodes a desired polypeptides of the present invention to produce transformed host cells; and maintaining the transformed host cells under biological conditions sufficient for expression of the polypeptide. Preferably, the transformed host cells are eukaryotic cells.

A host cell used in the process is capable of expressing a functional, recombinant peptide of the present invention. A variety of cells are amenable to a process of the invention, for instance, yeasts cells, human cell lines, and other eukaryotic cell lines well known to those of the art.

Following transfection, the cell is maintained under culture conditions for a period of time sufficient for expression of a peptide. Culture conditions are well known in the art and include ionic composition and concentration, temperature, pH and the like. Suitable medium for various cell types are well known in the art. In a preferred embodiment, temperature is from about 20° C. to about 50° C. pH is preferably from about a value of 6.0 to a value of about 8.0. Other biological conditions needed for transfection and expression of an encoded protein are well known in the art.

Transfected cells are maintained for a period of time sufficient for expression of the desired peptide. A suitable time depends inter alia upon the cell type used and is readily determinable by a skilled artisan. Typically, maintenance time is from about 2 to about 14 days.

A recombinant peptide having the ability to modulate programmed cell death is recovered or collected either from the transfected cells or the medium in which the cells are cultured. Recovery comprises isolating and purifying the recombinant polypeptide. Isolation and purification techniques for polypeptides are well known in the art and include such procedures as precipitation, filtration, chromatography, electrophoresis and the like.

G. Pharmaceutical Compositions

In a preferred embodiment, the present invention provides pharmaceutical compositions comprising cell death modulating peptides and a physiologically acceptable carrier. More preferably, a pharmaceutical composition comprises a polypeptide expressed by at least one mammalian Atg gene that is required for autophagic cell death including ATG7 (HsGSA7/mAPG7) or Beclin 1. A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g. injected intravascularly).

H. Therapeutics

In cancers where there is an increase in cell proliferation, it may be is desirable to increase the expression of a polypeptide expressed by at least one mammalian Atg gene required for autophagic cell death, including ATG7 (HsGSA7/mAPG7) or Beclin to limit cell proliferation. Preferably, the composition comprises a caspase 8 inhibitor. Therefore, in one embodiment, at least one autophagy inducing peptide may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

It is understood that modification that do not substantially affect the activity of the various embodiments of this invention are also included within the definition of the invention provided herein. Accordingly, the following examples are intended to illustrate but not limit the present invention.

4. Examples

Material and Methods

Reagents and Antibodies

Wortmannin, JNK inhibitor II (Anthra[1,9-cd]pyrazol-6 (2H)-one 1,9-pyrazoloanthrone), SB 203580, and PD 98059 were purchased from Calbiochem (San Diego, Calif.). Benzyloxycarbonyl-Valyl-Alanyl-Aspartyl-(O-methyl)-fluoromethylketone (zVAD), benzyloxycarbonyl-Phenyl-Alanyl-fluoromethylketone (zFA), benzyloxycarbonyl-Leucyl-Glutamyl-Histidyl-Aspartyl-fluoromethylketone (LEHD), benzyloxycarbonyl-Aspartyl-(O-methyl)-Glutamyl-(O-methyl)-Valyl-Aspartyl-(O-methyl)-fluoromethylketone (DEVD), and benzyloxycarbonyl-Alanyl-Alanyl-Aspartyl-(O-methyl)-chloromethylketone (zAAD) were purchased from Enzyme Systems Products (Livermore, Calif.). Cycloheximide, 3-methyladenine, and Phorbol myristate acetate were from Sigma (St Louis). Antibodies to mouse caspase-8, RIP, and Beclin-1 were purchased from Pharmingen (San Diego, Calif.). Antibodies to phospho-JNK, MKK7, and c-Jun were from Cell Signaling Technology (Beverly, Mass.). The Atg7 antibody was a gift from Dr. William Dunn.

Preparation of siRNA

Non-specific RNAi oligoribonucleotides and RNAi oligoribonucleotides corresponding to the following cDNA sequences were purchased from Dharmacon (Boulder, Colo.):

Mouse Sequences:

```
CAGTTTGGCACAATCAATA for beclin 1.    (SEQ ID NO: 5)

GTTTGTAGCCTCAAGTGTT for              (SEQ ID NO: 6)
mouse ATG7.

CCACTAGTCTGACTGATGA for RIP.         (SEQ ID NO: 7)

TGAGATACTCGAGGTGGAT for MKK7.        (SEQ ID NO: 8)

CATTCGATCTCATTCAGTA for c-Jun.       (SEQ ID NO: 9)

GATCGAGGATTATGAAAGA for caspase-8.   (SEQ ID NO: 10)

CAAGGAGTGGTGTTGTTAA for caspase-1.   (SEQ ID NO: 11)

CTTGTCTCTGCTCTTATGA for caspase-2.   (SEQ ID NO: 12)

TTAGCAAGATTTGGCGATA for caspase-3.   (SEQ ID NO: 13)

GACGTTGACTGGCTTGTTC for caspase-9.   (SEQ ID NO: 14)

TGACACGCTATTTCTACCT for              (SEQ ID NO: 15)
caspase-12.
```

Human Sequences:

```
CAGTTTGGCACAATCAATA for beclin 1.    (SEQ ID NO: 16)

GGAGTCACAGCTCTTCCTT for              (SEQ ID NO: 17)
human ATG7.
```

Transfection of siRNA 0.5 nmol RNAi were transfected by Amaxa nucleofection™, using V solution, program T-20 (Gaithersburg, Md.). Cells were then cultured in growth medium for 96 hrs before further analysis.

Tissue Culture

The mouse L929 cell line and human cell line U937 were obtained from the American Type Culture Collection (Rockville, Md.). Mouse RAW264.7 cells were a gift from Dr. Richard Siegel. L929 cells were cultured in Dulbecco's modified Eagle's medium with 4.5 g/L glucose. U937, RAW264.7 macrophage cells and mouse peritoneal macrophages prepared by thioglycollate injection were cultured in RPMI 1640 medium. Media were supplemented with 2 mM L-glutamine, 1% penicillin/streptomycin solution, and 10% fetal bovine serum (FBS).

Cell Death Analysis

Cell viability was determined after treatments by staining with propidium iodide (2 µg/mL) and flow cytometric analysis on a FACScan. Percent cell death was quantitated as previously described (26).

Detection of the Phosphorylated JNK/SAPK

L929 cells were treated with DMSO or zVAD for 24 hrs in the presence of 2% FBS. The cell lysate was spun for 10 minutes at 13000 rpm. 20 ul of the c-Jun beads (SAPK/JNK assay kit from Cell Signaling) were added to the supernatant and incubated overnight at 4° C. Beads were washed 4 times with lysis buffer and resuspended in 50 ul of 1× sample buffer. Samples were boiled for 5 minutes and analyzed by SDS-PAGE and Western blot for phosphorylated SAP/JNK by probing with phospho-JNK antibody.

Electron Microscopy Analyses

Cells were fixed in 3% glutaraldehyde in 0.1 M MOPS buffer (pH 7.0) for 8 hrs at room temperature, 3% glutaraldehyde/1% paraformaldehyde in 0.1 M MOPS buffer (pH 7.0) for 16 hours at 4° C., post-fixed in 1% osmium tetroxide for 1 hour, embedded in Spurr's resin, sectioned, double stained with Uranyl acetate and Lead citrate, and analyzed using a Zeiss EM 10 transmission electron microscope. For each treatment or control group, at least 100 cells from randomly chosen transmission electron microscopy fields were analyzed for quantification of morphological features. Cells with ≧10 vacuoles were scored as autophagy positive. Cells were stratified as follows: 0 (≦9 vacuoles/cell), 1(10-19 vacuoles/cell), 2 (20-29 vacuoles/cell), 3 (≧30 vacuoles/cell). Scores were ranked and comparisons of treatment to control groups were made using the Mann-Whitney U test using the Statview 5.0.1 program. Statistical analysis of the differences in FIG. 1, panels D, E, F, and G and FIG. 2A, B, D were significant (p<0.0001).

Example 1

Autophagy and ATG Genes are Required for zVAD-Induced Cell Death.

Figure 1B:
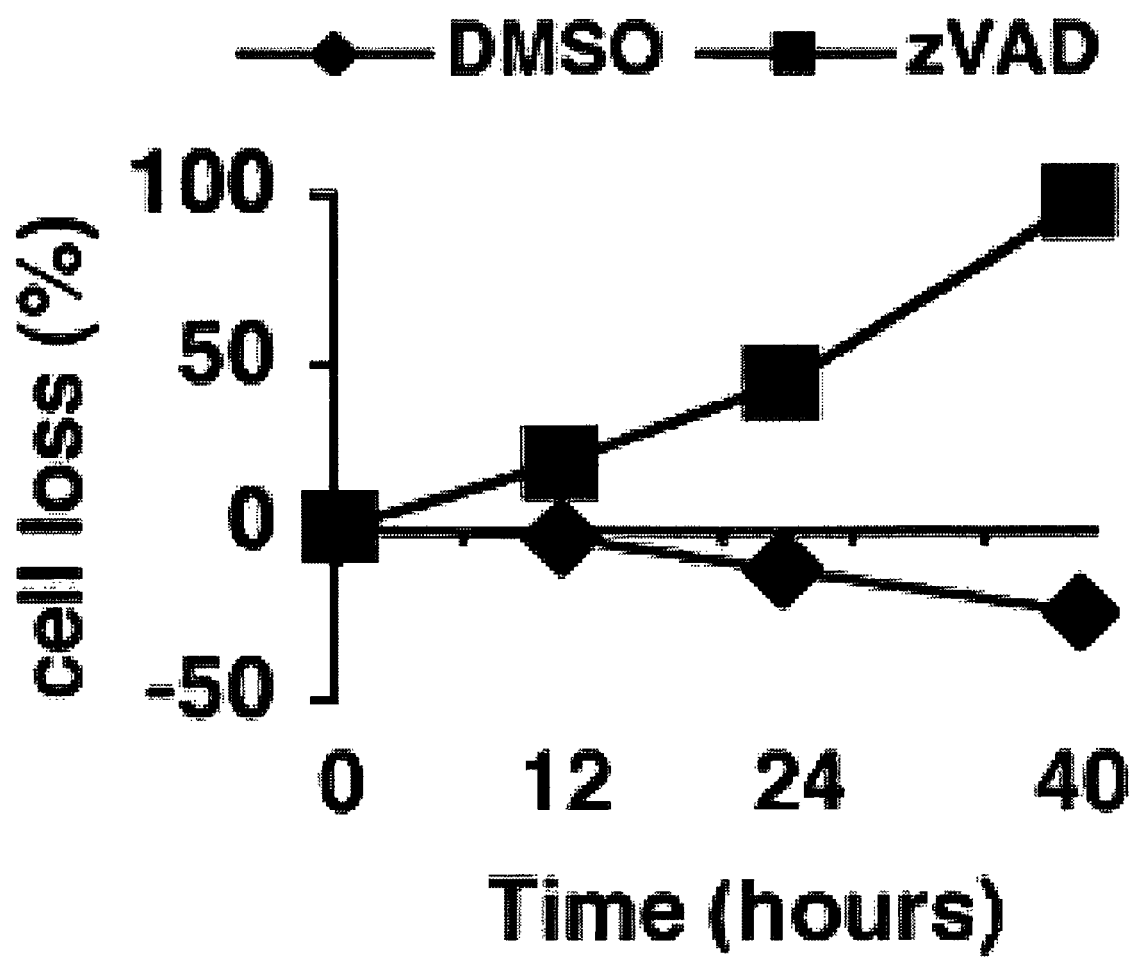
Figure 1C:
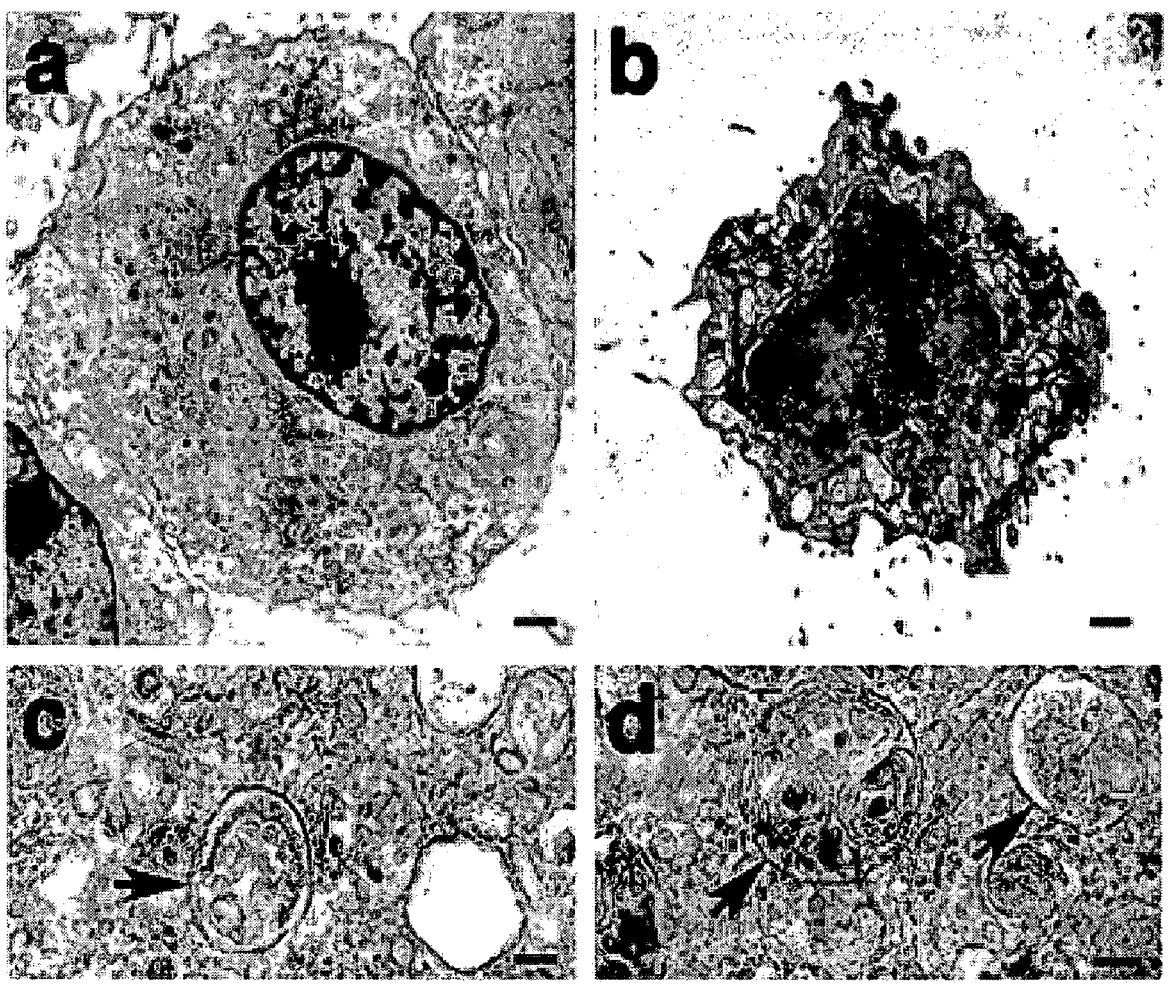
Figure 1D:
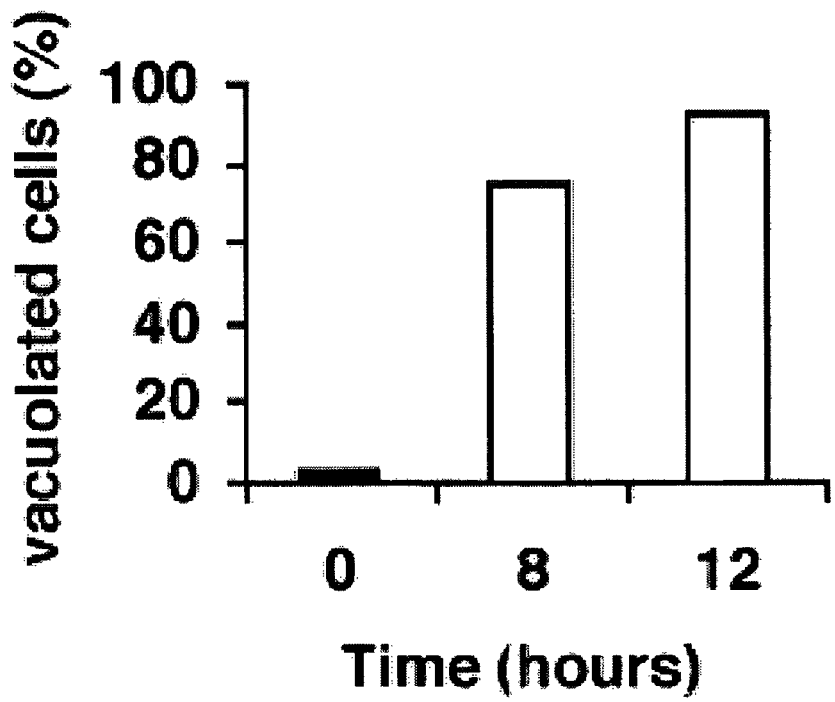
Figure 4:
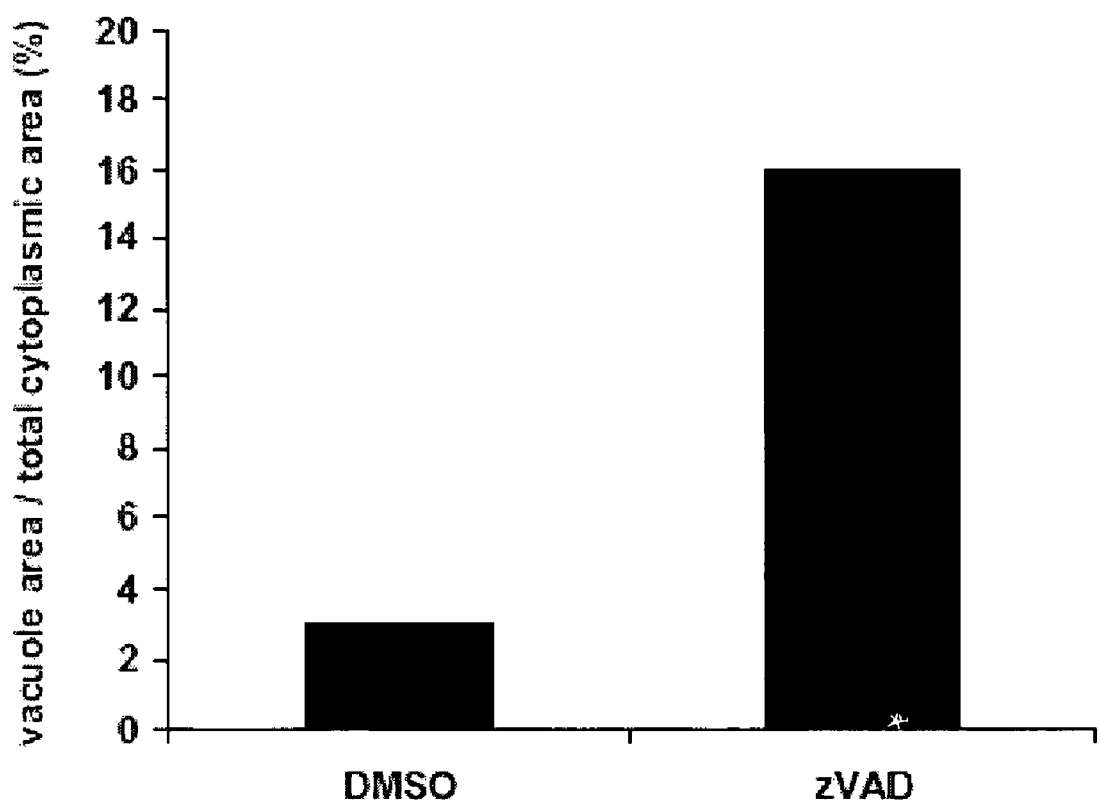
FIG. 4 shows morphometric analyses of L929 cells treated with DMSO or zVAD.

In mouse L929 fibroblastic cells, tumor necrosis factor (TNF), oxidants, ceramide, and radiation can induce caspase-independent death (11). However, benzyloxycarbonyl-Valyl-Alanyl-Aspartic-acid (O-methyl)-fluoromethylketone (zVAD), a caspase inhibitor with broad specificity, also directly induced the death of L929 cells. L929 cells were treated with 1 ul of dimethyl sulfoxide (DMSO) FIG. 1A (a and c) or 20 uM zVAD (b and d) for 24 hours and examined by phase contrast microscopy (a and b); or 4',6'-diamidino-2-phenylindole-staining and fluorescent microscopy (c and d). Magnification: 200×. Death began at 12 hours after zVAD treatment and was complete after 40 hrs as shown in FIG. 1B. Transmission electron microscopy (TEM) revealed intact mitochondria and endoplasmic reticulum, condensed osmophilic cytoplasm, and numerous large cytoplasmic inclusions that were membrane-bound vacuoles characteristic of autophagy as shown in FIG. 1C where (a) shows cell treated with DMSO and (b to d) treated with zVAD. The dead cells appeared to be round, detached, and had a convoluted plasma membrane permeable to vital dyes; this differed from apoptosis in which nuclei are condensed and membrane integrity is preserved. A time course for zVAD induced autophagy revealed that vacuolated cells accumulated prior to cell death as shown in FIG. 1D. The percentage of vaculated cells is the fraction of cells that have 10 or more autophagic vacuoles by TEM. Statistical analysis is shown in FIG. 4 and morphometric analysis of zVAD-induced autophagy in L929 cells is quantitated in Table 1 setforth below.

TABLE 1

|  | ZVAD 0 hrs | ZVAD 8 hrs | ZVAD 12 hrs |
|---|---|---|---|
| Normal cells | 85 | 19 | 2 |
| Autophagic cells(total) | 0 | 76 | 93 |
| Mild autophagy (cell with 10~19 vacuoles) | 0 | 55 | 24 |
| Moderate autophagy (cell with 20~29 vacuoles) | 0 | 20 | 59 |

TABLE 1-continued

|  | ZVAD 0 hrs | ZVAD 8 hrs | ZVAD 12 hrs |
|---|---|---|---|
| Severe Autophagy (cell with 30 or more vacuoles) | 0 | 1 | 10 |
| Apoptotic cell | 0 | 4 | 1 |
| Autophagic and apoptotic features | 0 | 1 | 1 |
| Lytic/necrotic cell | 0 | 0 | 3 |
| Vacuolated(but not autophagic) | 15 | 0 | 0 |
| Total | 100 | 100 | 100 |

Figure 5:
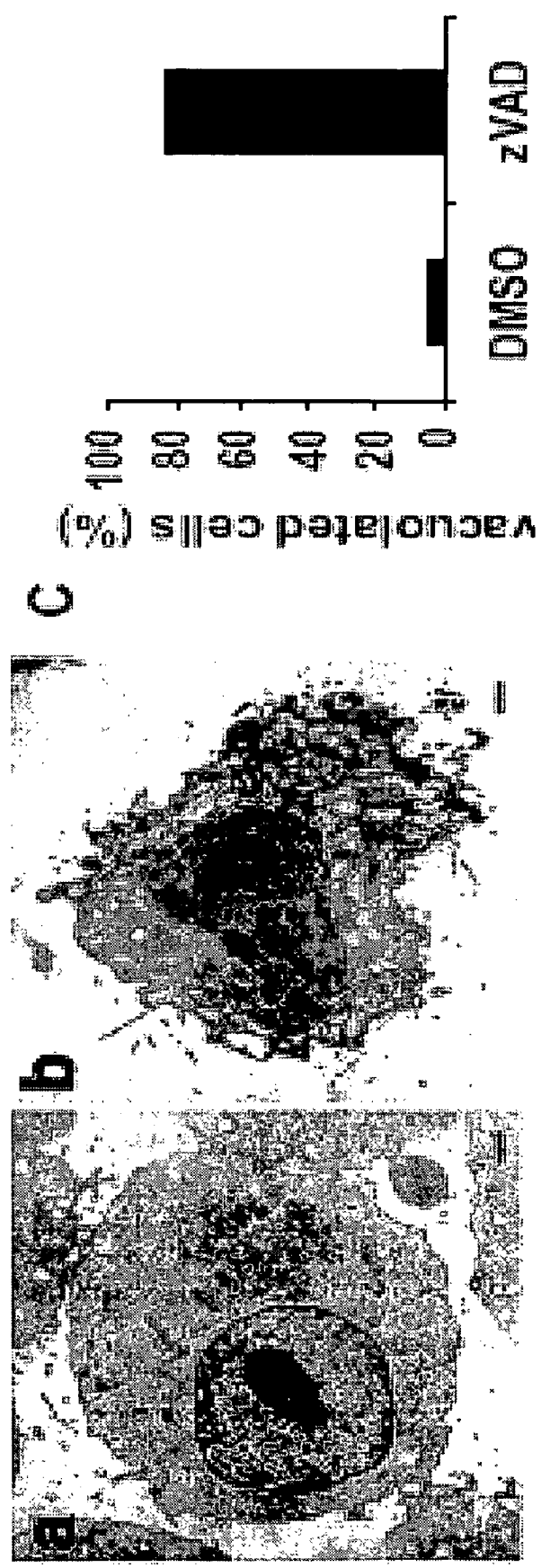
FIG. 5 shows transmission electron microscopy (TEM) of U937 cells treated for 24 hours with DMSO (a) or zVAD (b). Scale bar in (a, b), 1 um; (c) and quantitated as described for FIG. 1.

Similar results were shown when using U937 monocytoid cells with the results shown in FIG. 5, wherein TEM of U937 cells treated for 24 hours with DMSO (a) or zVAD (b). Scale bar in (a, b), 1 um; (c) wherein the fractions of cells with autophagic features based on TEM were quantitated as described above.

Figure 1E:
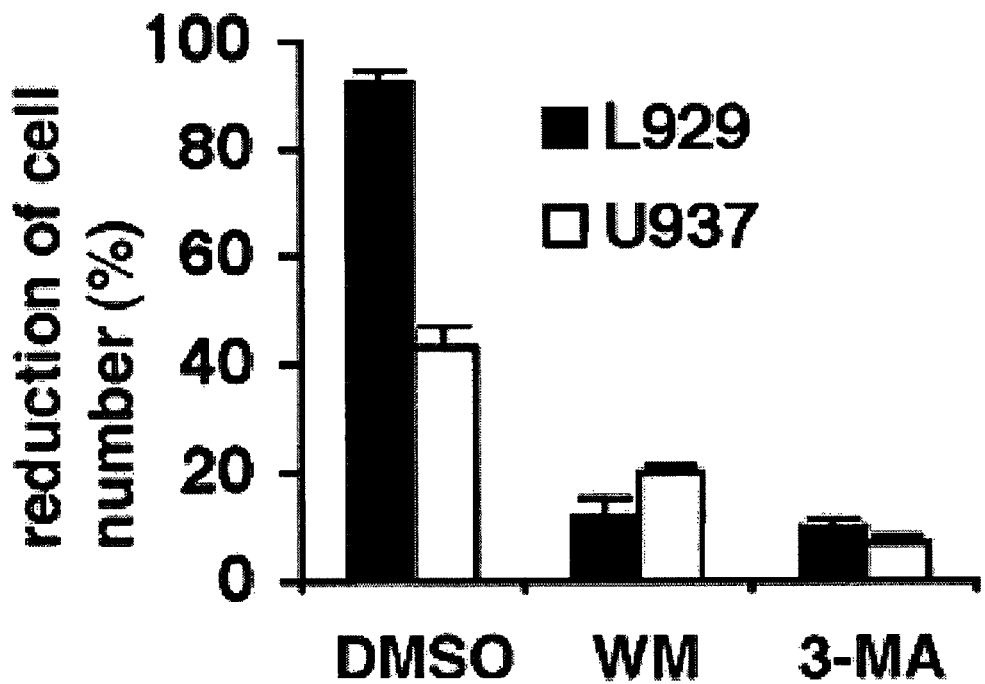

The association of autophagic vacuoles with cell death has been observed in developing animals, but it has not been clear if it was a process to rescue or condemn the cell (12). *Drosophila* cells manifesting autophagy and death have increased ATG gene transcripts (13, 14), but heretofore there was no known requirement for ATG genes in cell death. As such, evidence was sought to show that autophagy was required for cell death by treating cells with two inhibitors of autophagy, 3-methyladenine (3-MA) and Wortmannin (9, 15). FIG. 1E shows that the reduction in cell loss (mean value±SD) for L929 cells treated with the PI-3 kinase inhibitors Wortmannin (WM) (0.1 ug/ml) or 3-MA (10 mM0 for 1 hour and then with 20 uM zVAD for 36 hours. Clearly, by treating the cells with an autophagic inhibitor, there was reduced less cell death relative to the cells treated with zVAD dissolved in DMSO.

Figure 6:
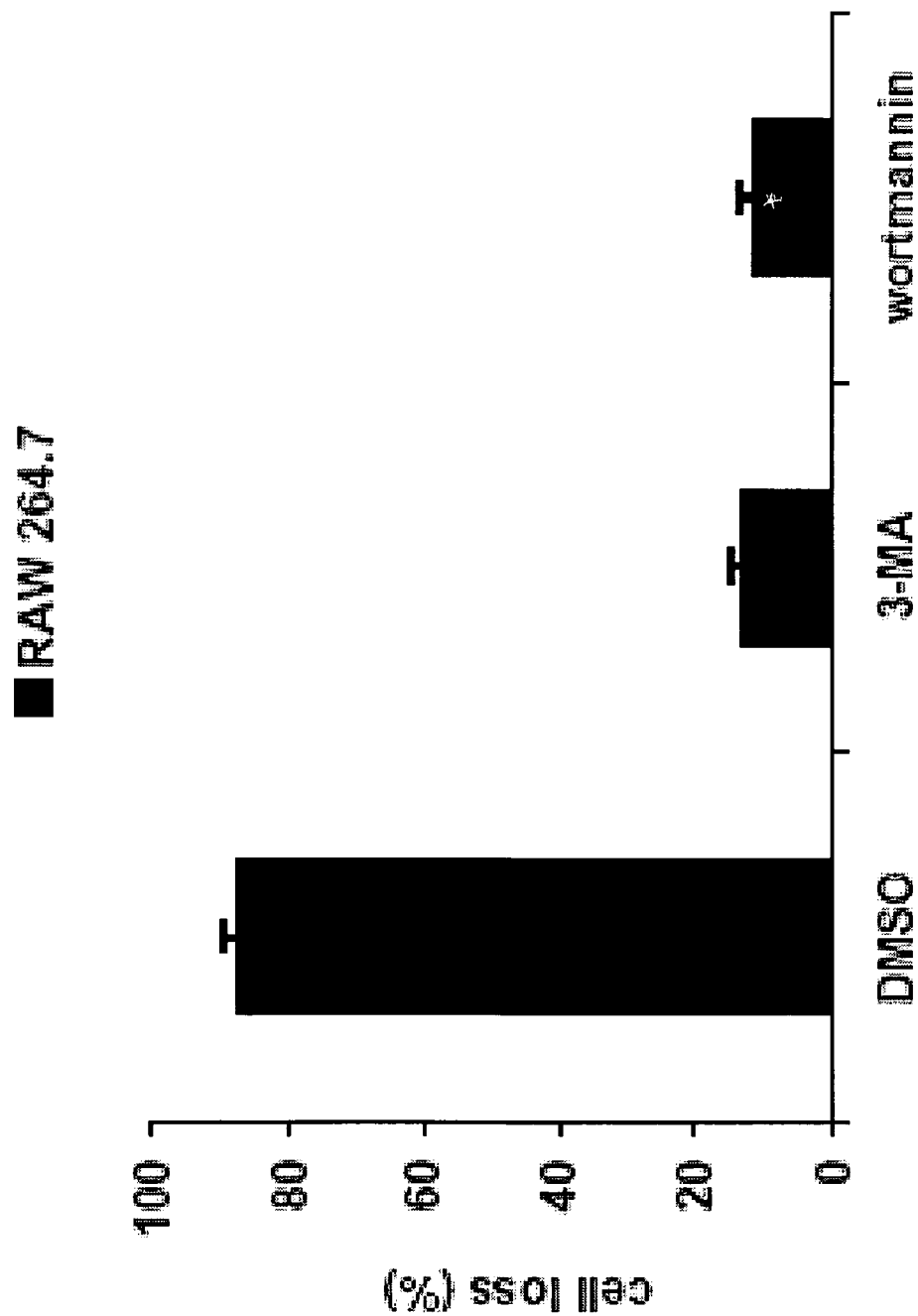
FIG. 6 shows that zVAD induces cell death in RAW264.7 cells and can be blocked by autophagy inhibitors.
Figure 7:
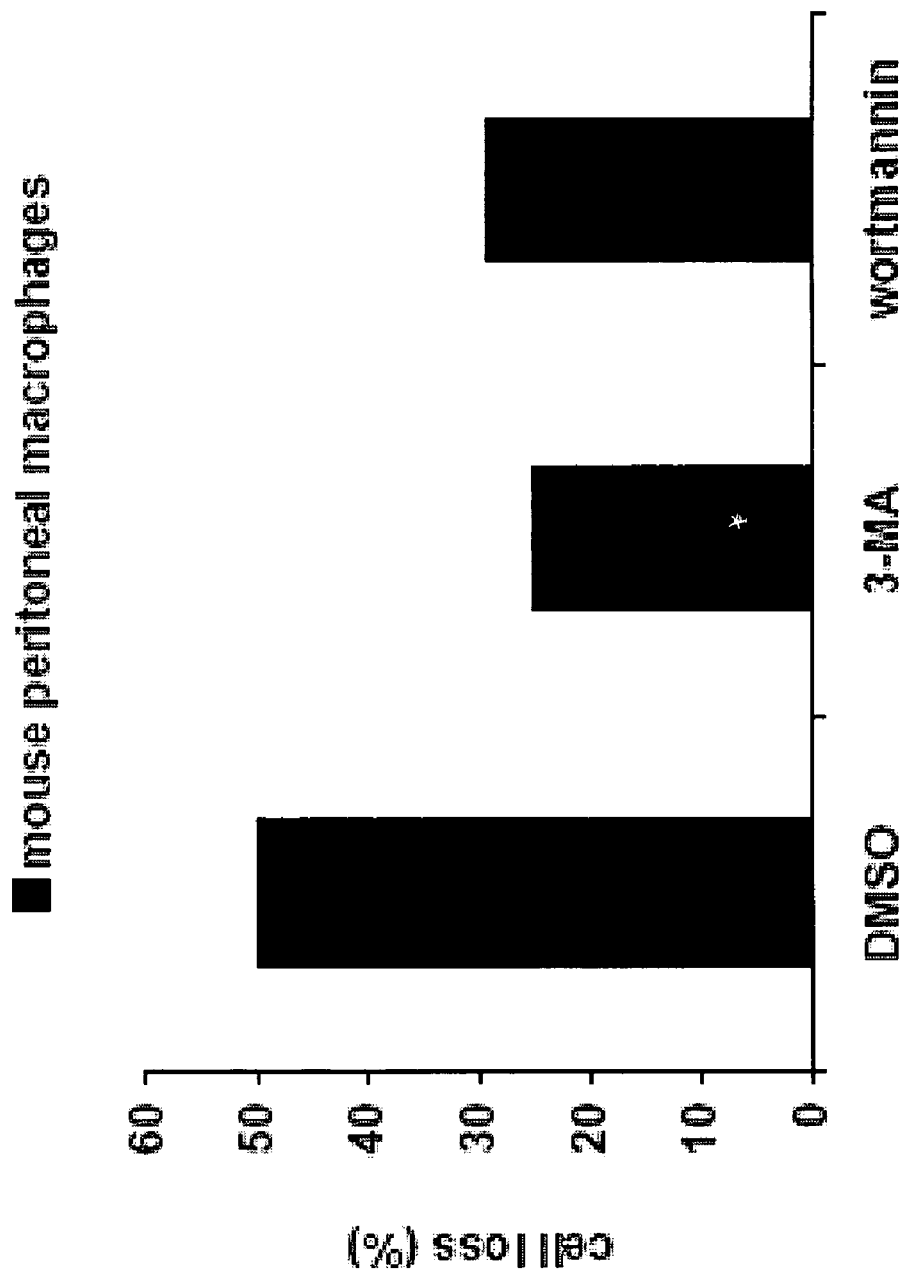
FIG. 7 shows that zVAD induces cell death in mouse peritoneal macrophages and can be blocked by autophagy inhibitors.

Further, zVAD also induced cell death by the autophagic pathway in mouse RAW 264.7 macrophage cells and primary mouse peritoneal macrophages as shown in FIGS. 6 and 7. Both inhibitors, WM and 3-MA arrested zVAD-induced cell death in these cell lines and in primary macrophages as shown in FIGS. 6 and 7. Specifically FIG. 6 shows that zVAD induces cell death in RAW264.7, which can be blocked by autophagy inhibitors. The RAW264.7 cells were treated with 0.1 ug/ml Wortmannin (WM) or 10 mM 3-methyladenine (3-MA) for 1 hr and the with 100 uM zVAD for 48 hrs, after which cell loss was quantitated by flow cytometry. The first bar shows the results of cells treated with zVAD dissolved in DMSO. Further, FIG. 7 shows that zVAD induces cell death in mouse peritoneal macrophages, which can be blocked by autophagy inhibitors. Mouse peritoneal macrophages cells were treated with 0.1 ug/ml Wortmannin (WM) or 10 mM 3-methyladenine (3-MA) for 1 hr and with 100 uM zVAD for 24 hrs, after which cell loss were quantitated by flow cytometry. Again, it is evident that the autophagic inhibitors reduced cell death by the autophagic pathway while the autophagic pathway was in full force in the cells treated with zVAD dissolved in DMSO.

Figure 1F:
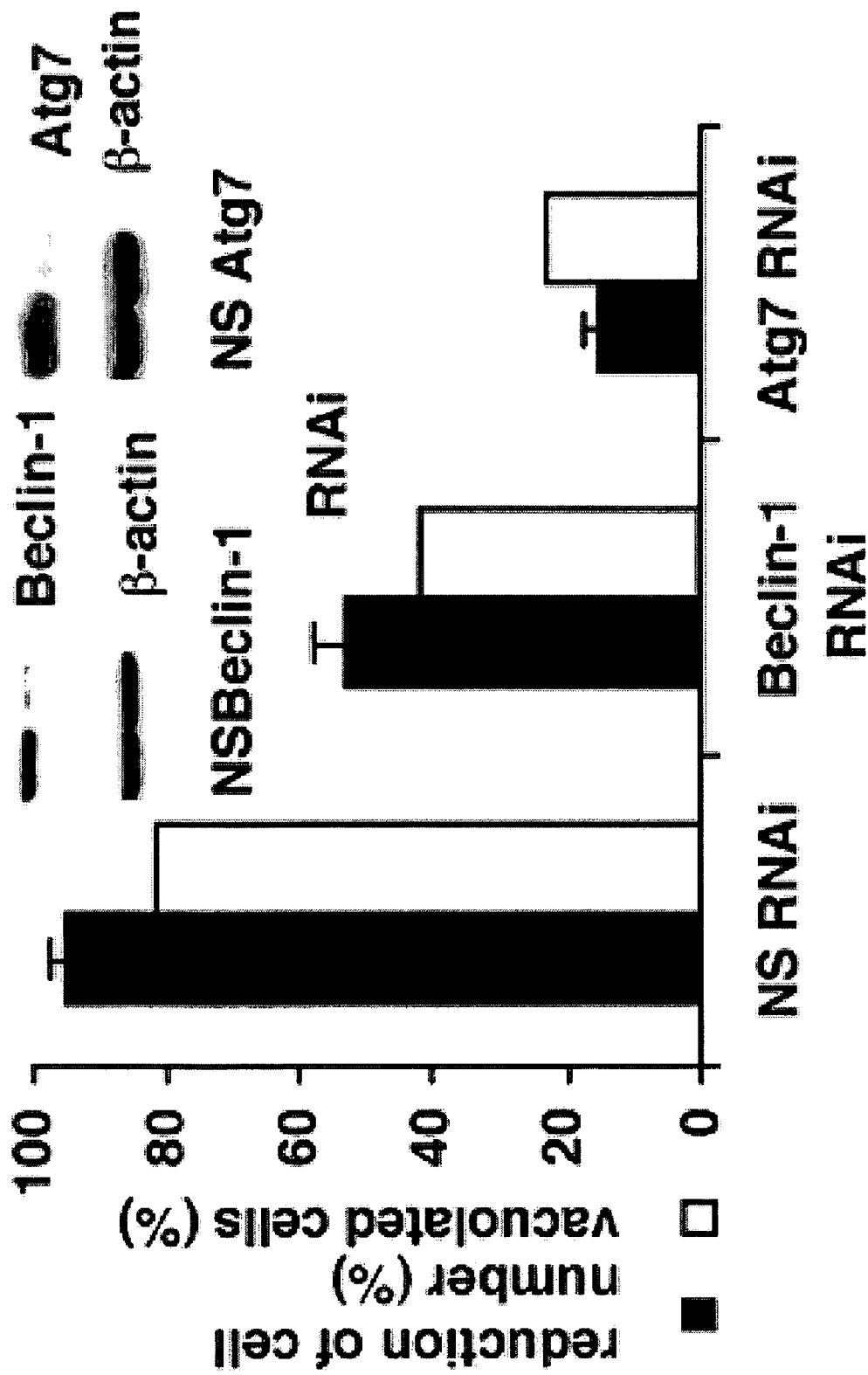

However, these inhibitors are general phosphatidylinositol-3 kinase (PI-3 kinase) inhibitors and could independently affect autophagy and non-apoptotic cell death. Therefore, tests were conducted to determine whether ATG genes were required for cell death. L929 cells were treated for 36 hours with zVAD or DMSO after transfection with beclin 1, ATG7 (mAPG&) RNAi, or nonspecific (NS) oligoribonucleotides, and reduction in cell number (solid bar) and vaculated cell (open bars) were quantified. As shown in FIG. 1F, expression of ATG7 was reduced by RNAi and it can be seen that zVAD-induced cell death was almost completely inhibited. Further, reduction of the expression of Beclin-1 protein by RNAi also decreased zVAD-induced death. Reduction in the corresponding protein can be seen in the Western blot (inset).

Figure 1G:
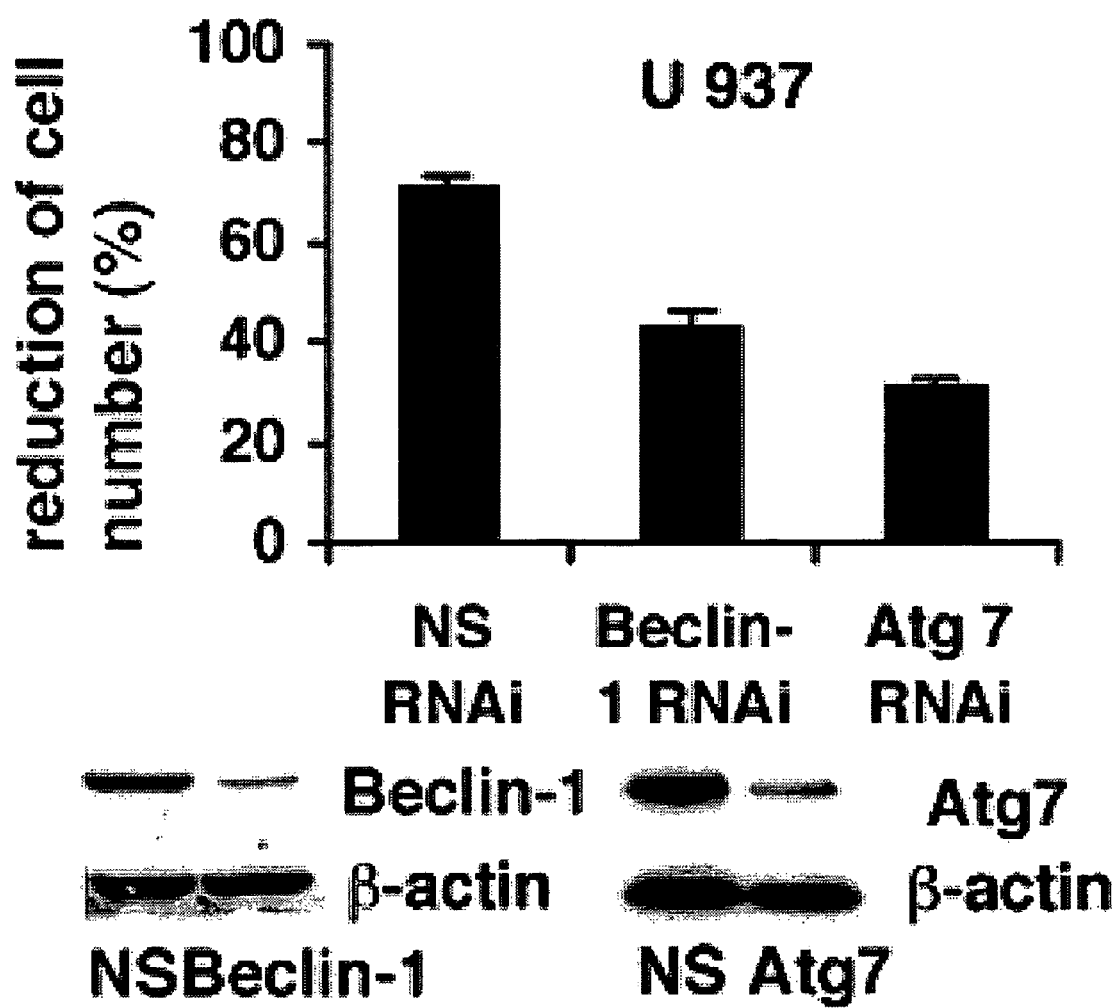

Reduction of the expression of ATG7 and beclin 1 also inhibited zVAD-induced death in human U937 cells as shown in FIG. 1G. U937 cells were activated by 10 ng/ml phorbol myristat acetate for 24 hours after transfection with beclin 1, ATG7(hGSa7) RNAi, or nonspecific (NS) oligoribonucleotides, and then reduction in cell numbers was measured after zVAD treatment for 36 hours.

Figure 1H:
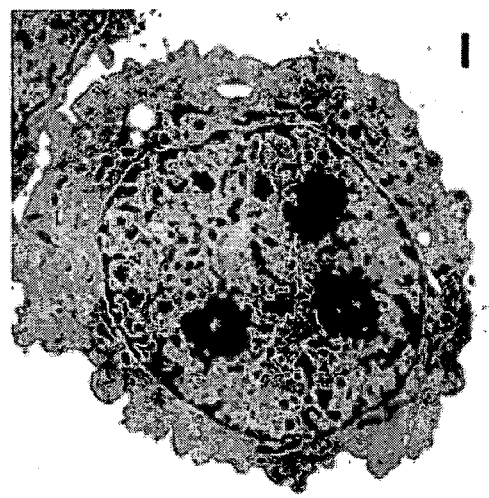
Figure 1H:
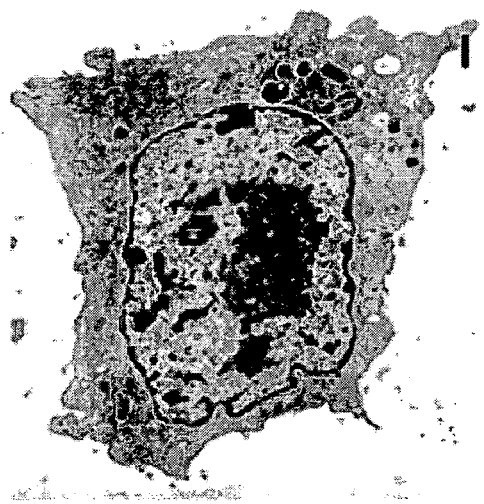
Figure 1H:
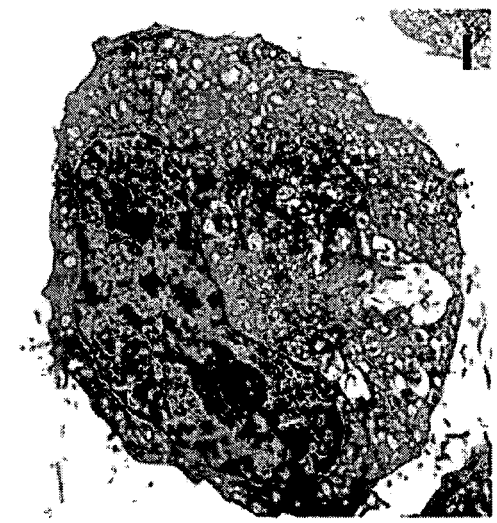

TEM analyses of cells with reduced Atg7 or Beclin-1 protein levels showed a parallel inhibition of autophagic vacuole formation associated with reduced cell death as shown in FIG. 1H. FIG. 1H provides representative TEM photomicrographs of the L929 cells treated with zVAD (24 hours) and with the indicated RNAi preparations. The fractions of cells with autophagic features based on TEM were quantitated and the data set forth in Table 2.

TABLE 2

| Sample | NS RNAi | U937 Beclin-1 RNAi | U937 ATG7 RNAi |
|---|---|---|---|
| Normal | 14 | 40 | 51 |
| Autophagic cells | 79 | 53 | 42 |
| Apoptotic cells | 2 | 4 | 3 |
| Lytic/necrotic cells | 5 | 3 | 4 |
| Vacuolated cells | 0 | 0 | 0 |
| TOTAL | 100 | 100 | 100 |

Thus, thus expression of the Atg7 and Beclin-1 genes is required for nonapoptotic cell death triggered by zVAD.

Example 2

Requirement of RIP and JHK Signaling Pathways for Autophagic Death

Figure 2A:
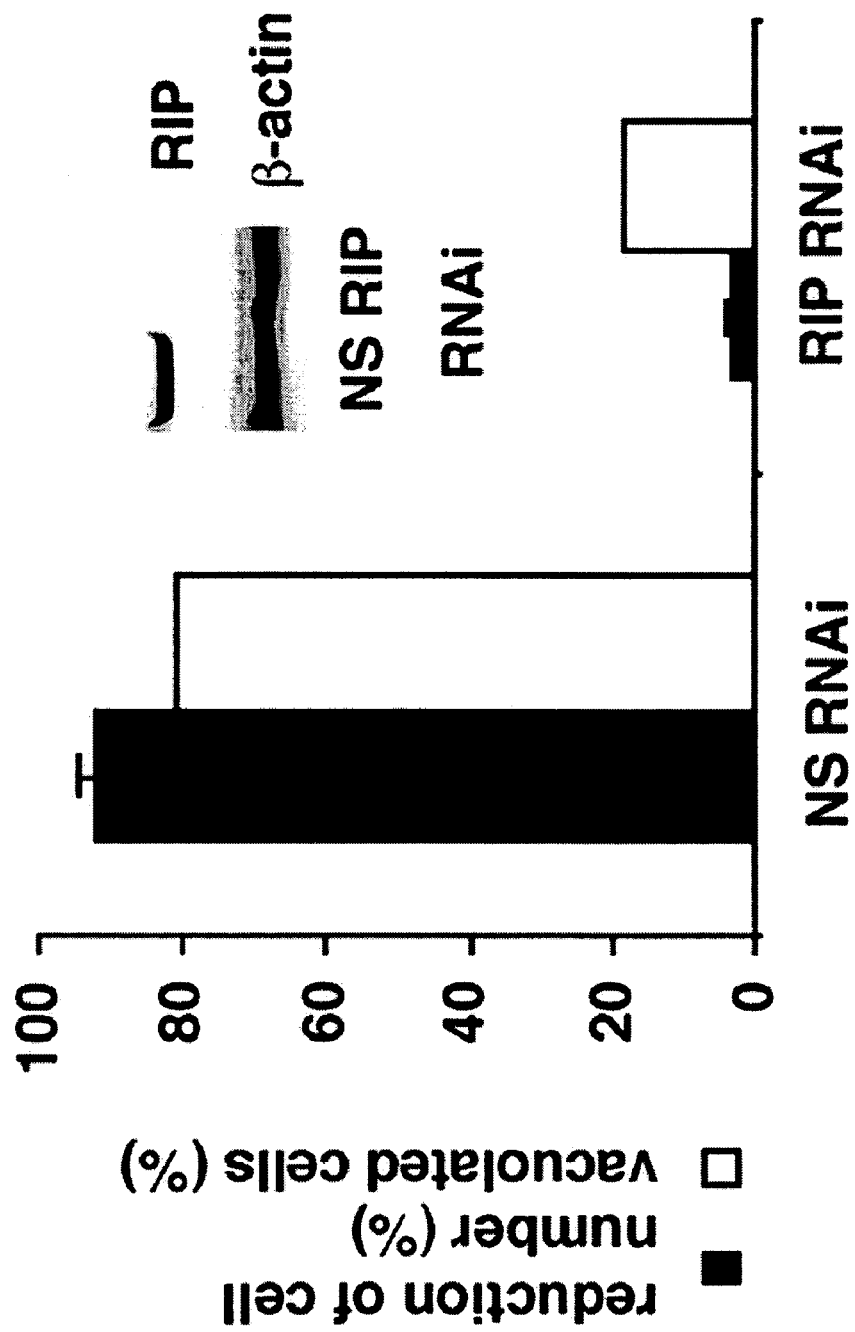
FIGS. 2 A-D show the requirement of RIP and JNK signaling pathways for autophagic death.
Figure 2B:
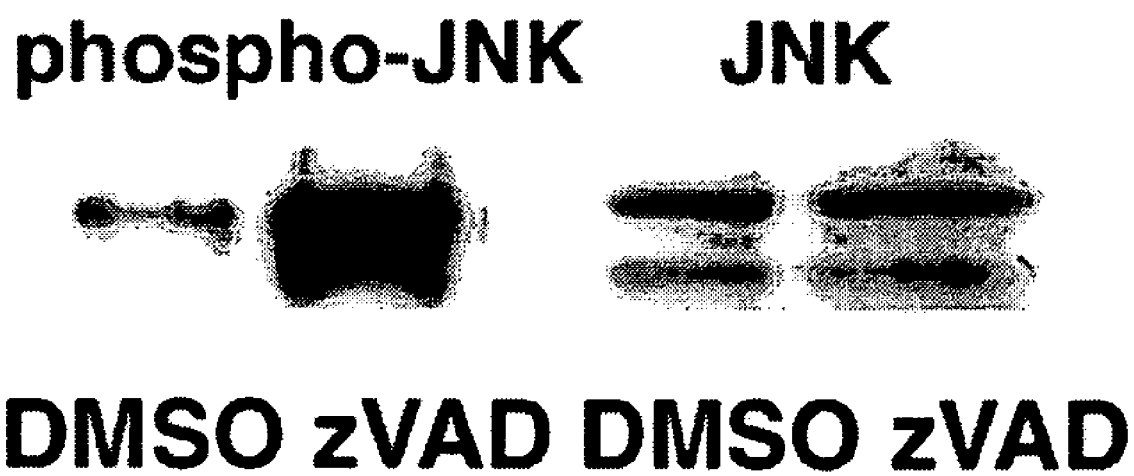

Death receptors can elicit nonapoptotic death through the "receptor-interacting protein" (RIP), a death-domain-containing, serine-threonine kinase (6, 7). RIP expression was reduced by RNAi and decreased autophagy and cell death was observed. For example, cells were treated with zVAD after transfection with RIP RNAi or nonspecific (NS) oligonucleotides. Reduction in cell number (solid bars) and the fractions of cells with autophagic features based on TEM (open bars) are shown in FIG. 2A. FIG. 2B is a western blot for phospho-JNK (left lane) or total JNK protein (right lane) after zVAD treatment. zVAD activated c-Jun N-terminal kinase (JNK) that is also activated by RIP in response to cytokines.

Figure 2C:
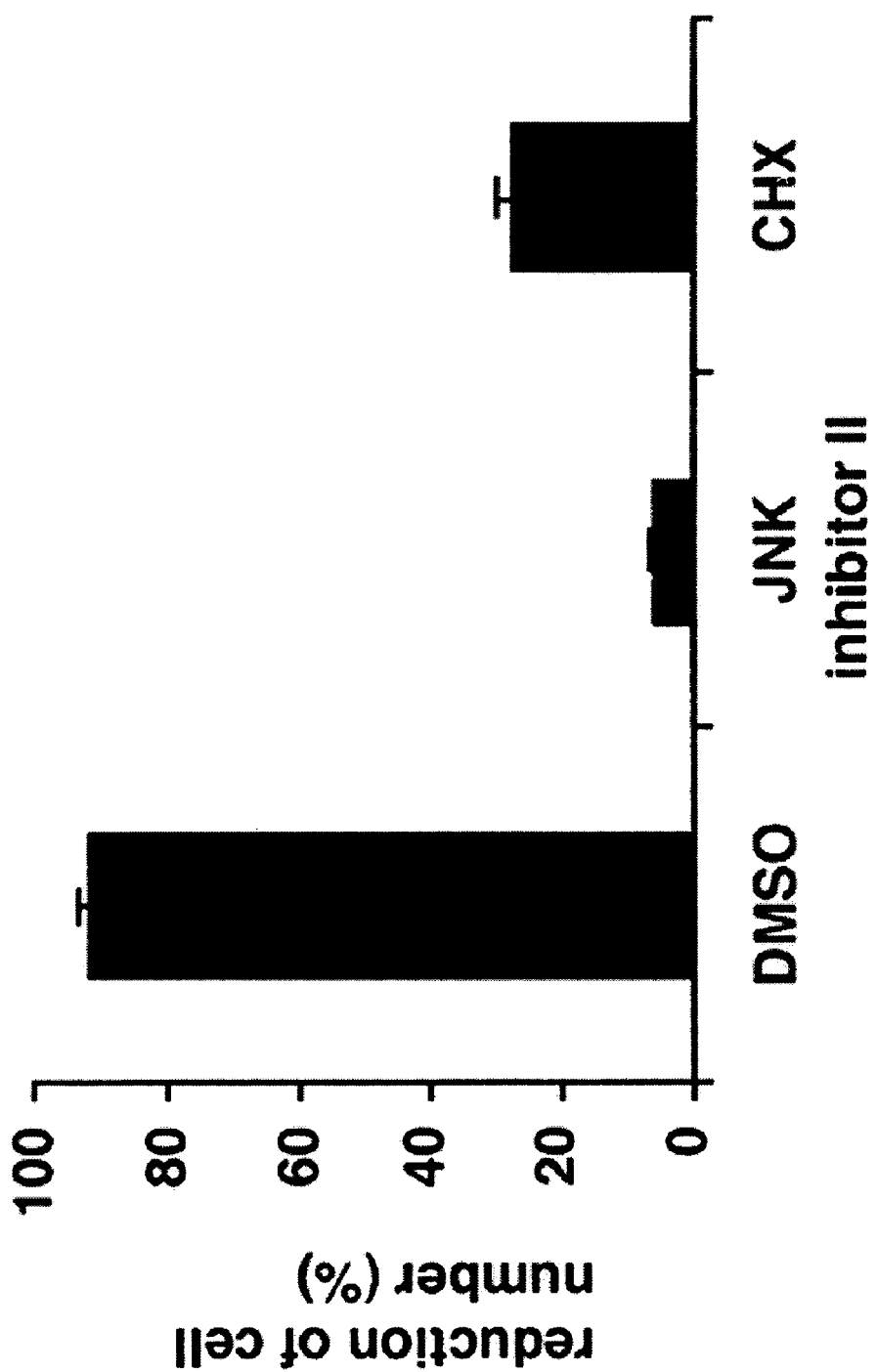
Figure 8:
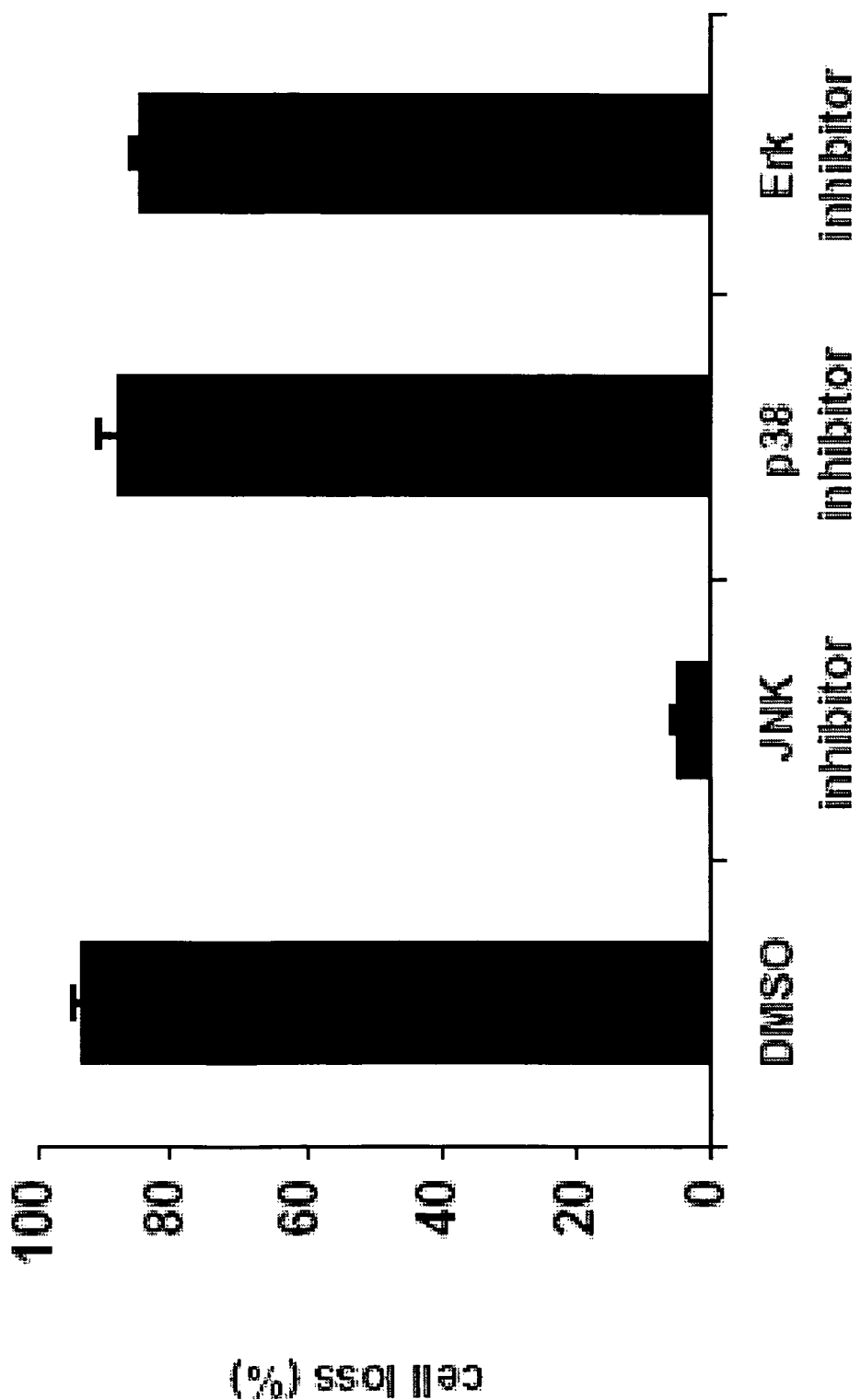
FIG. 8 shows that p38 and Erk signaling are not involved in zVAD induced L929 cell death.

L929 cells were pretreated with 1 ug/ml JNK inhibitor II, 1 ug/ml p38 inhibitor SB 203580, or 1 ug/ml Erk inhibitor PD 98059 for 1 hour, and were then treated with 20 uM zVAD for 40 hours, with zVAD dissolved in DMSO as a control. % cell loss was quantified by flow cytometry, By viewing FIG. 8 it can be seen that the JNK inhibitor, but not inhibitors against p38 or Erk, blocked zVAD-induced cell death, further indicating a specific role for JNK. Further, the protein synthesis inhibitor cycloheximide (CHX) blocked cell death, indicating that protein synthesis was required as shown in FIG. 2C.

Figure 2D:
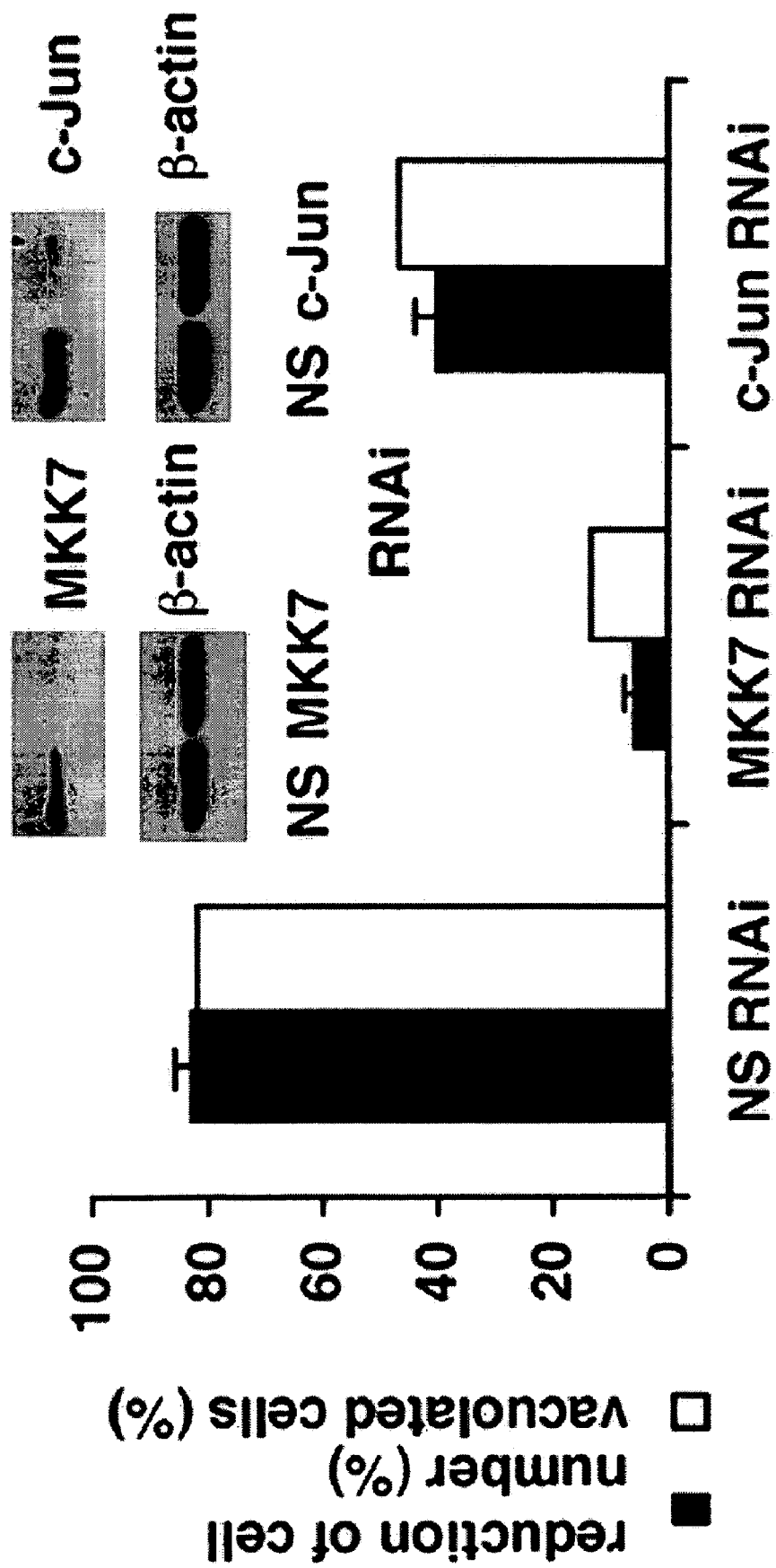

Reduction in cell number was quantified and shown in FIG. 2D following zVAD treatment for 36 hours after transfection with MKK7 RNAi, c-jun RNAi, or nonspecific oligoribonucleotides (solid bars) and the fractions of cells with autophagic features by TEM (open bars). RNAi silencing of the JNK-activating kinase MKK7 (MAP kinase 7) also completely prevented cell death and formation of autophagic vacuoles as shown in FIG. 2D. The steady-state amounts of the corresponding proteins are shown by Western blot (inset). RNAi suppression of the transcription factor c-Jun reduced but did not eliminate the c-Jun protein and inhibited autophagy and cell death by 45 to 50%. Thus, a signal pathway involving RIP, MKK7, JNK, and c-Jun appears to activate autophagy and cell death. The involvement of c-Jun and new protein synthesis implies transcription of target genes may also be required.

Example 3

Inhibition of the Autophagic Death Pathway by Caspase-8

Figure 3A:
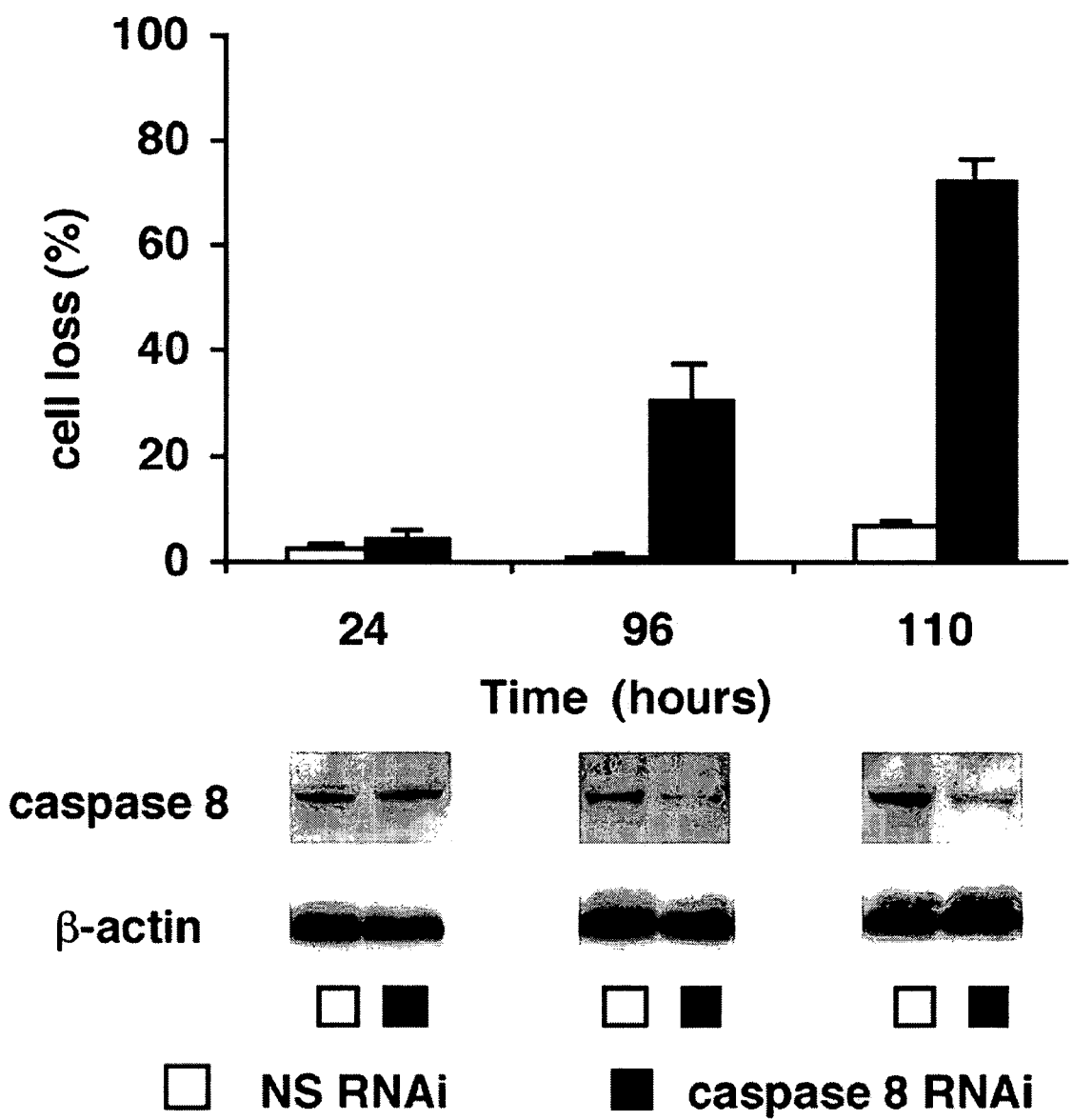
FIGS. 3 A-B show the inhibition of the autophagic death pathway by caspase-8.

Finally, the mechanism as to how zVAD induced autophagic cell death was investigated. RNAi was used to progressively reduce caspase-8 expression over time. FIG. 3A shows the time course of viability of L929 cells transfected with either nonspecific (NS) (open bars) or caspase 8-specific (solid bars) RNAi at 24, 96, and 110 hours after transfection. It was found that cell death was correspondingly increased by inhibiting the expression of caspase 8 and thereby inducing the autophagic pathway. Inset panels show the abundance of caspase-8 protein by Western blot.

Figure 3B:
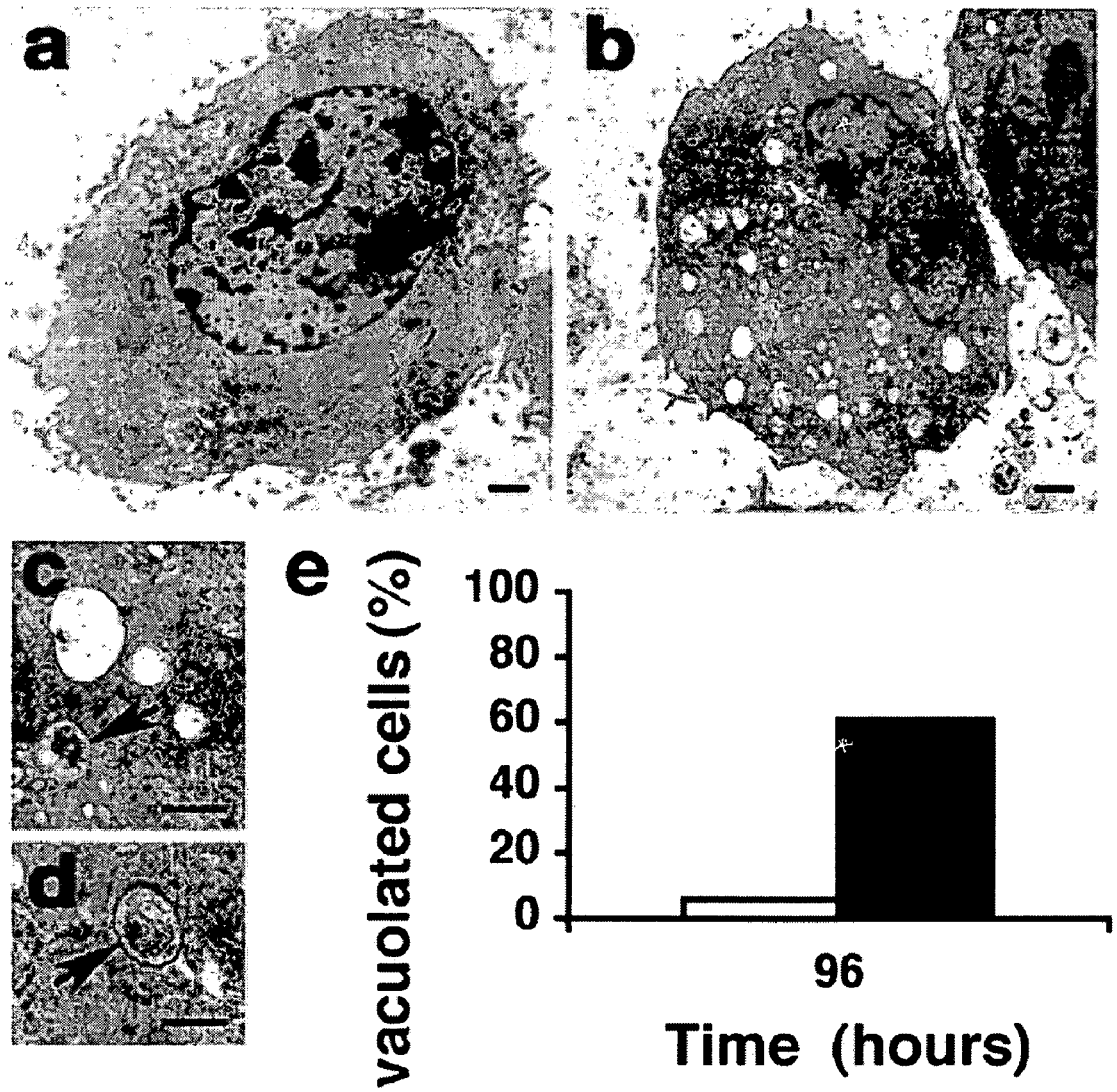

Representative TEM pictures and quantification of the cells treated with either nonspecific or caspase-8 specific RNAi showed features of autophagy. Cells were harvested at 96 hours after RNAi transfection (a) NS control cell, (b to d) Caspase-8 RNAi at different magnifications. The arrows in c and d show double-membrane autophagic vacuoles. FIG. 3B(e) shows the fraction of cells with autophagic features based on TEM. The (NS) control cell (open bar) and the caspase-8 RNAi (solid bar).

Figure 9:
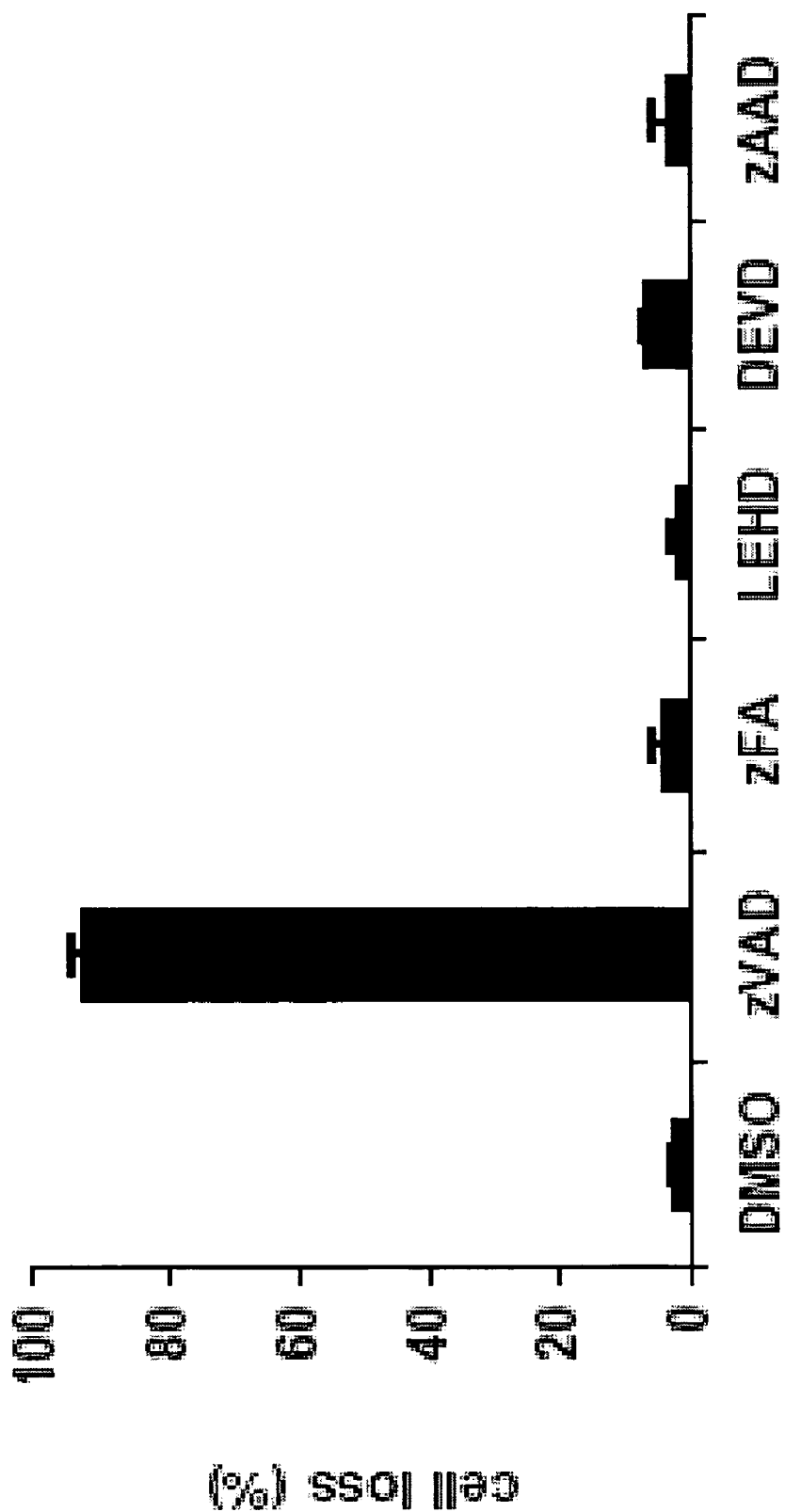
FIG. 9 shows induction of L929 cell death by numerous caspases inhibitors.
Figure 10:
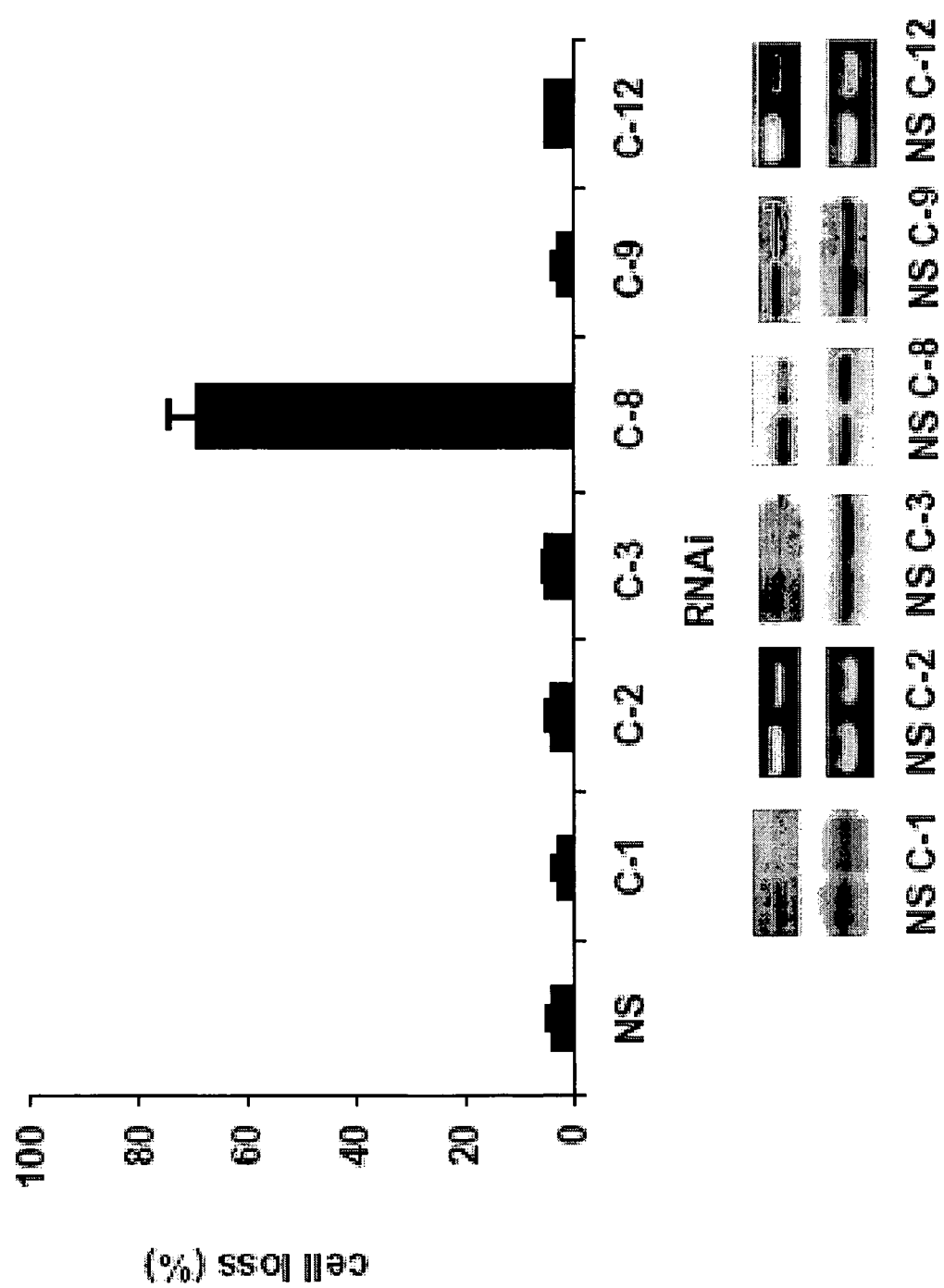
FIG. 10 shows induction of L929 cell death by caspase RNAi. L929 cells were transfected with caspase-1, caspase-2, caspase-3, caspase-8, caspase-9, caspase-12 or nonspecific (NS)RNAi.

Other peptide caspase inhibitors such as zFA, LEHD, DEVD, or ZAAD had no ability to induce cell death as shown in FIG. 9. L929 cells were treated with 1 ul/ml DMSO, 20 uM zVAD, 20 uM zFA, 20 uM LEHD, 20 uM DEVD, or 20 uM zAAD for 40 hours, and % cell loss was quantified by flow cytometry. Clearly none of the other inhibitors or DMSO induced cell death except the caspase 8 inhibitor. Further, RNAi suppression of caspases 1, 2, 3, 9, and 12 had no ability to induce death as shown in FIG. 10. Because zVAD is a potent inhibitor of caspase-8, it likely exerted its death effect through inhibition of caspase-8.

Figure 11:
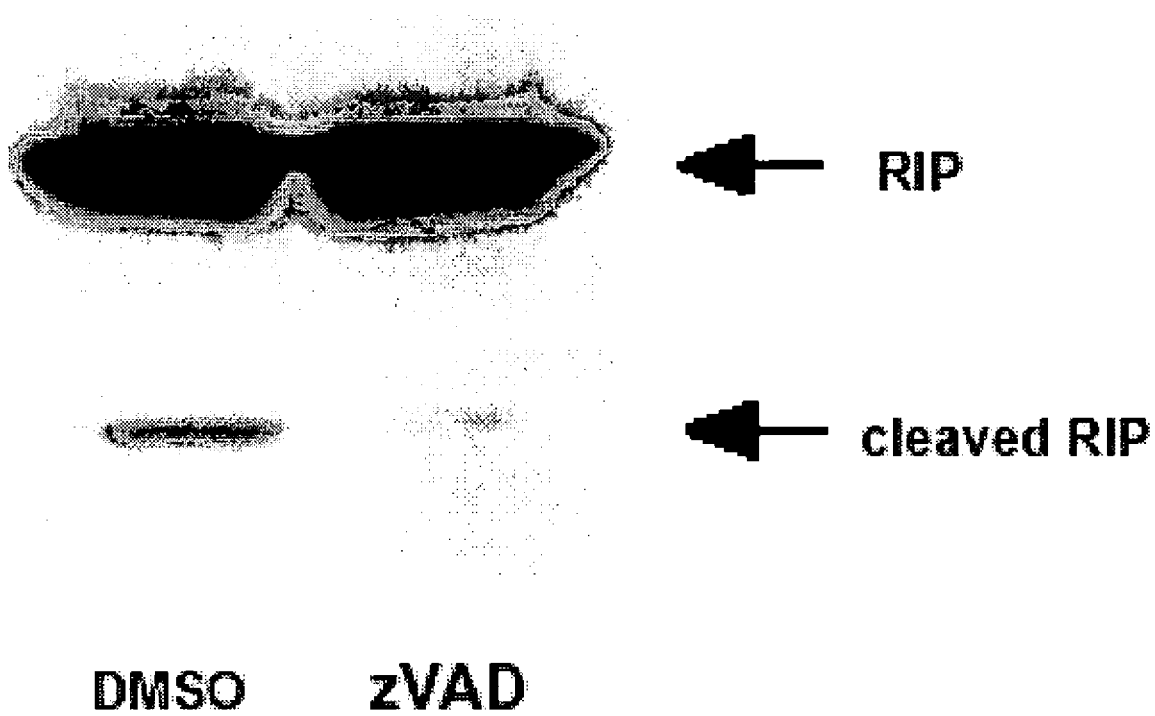
FIG. 11 shows that zVAD treatment prevents RIP from constitutive caspase-8 cleavage.

It was observed that the signaling through the serine-threonine kinase RIP is essential for autophagic cell death. When RIP is cleaved and inactivated by caspase 8, then a mechanism is provided for the prevention of autophagic cell death. However, inhibition of caspase 8 allows RIP to transmit the signal needed to kill the cell through the autophagic pathway. FIG. 11 shows that RIP was partially cleaved into fragments which is characteristic of caspase-8 activity in the cells, however no cleaved fragments were found in cells that were treated with the caspase 8 inhibitor zVAD. Clearly, zVAD treatment prevents RIP from constitutive caspase-8 cleavage. The indicated band is the 42 kD proteolytic product that is characteristic of caspase-8 cleavage (1).

The results shown herein indicate that two key autophagy genes, ATG7 and beclin 1, are necessary for a non-apoptotic death pathway in mammalian cells. The conservation of autophagy genes throughout phylogeny suggests that this form of death has a role in many eukaryotes. The suppression of autophagic death by caspase-8 in mammalian cells indicates caspases can regulate both apoptotic and non-apoptotic cell death. Because viral pathogens and cancer tumor cells have caspase inhibitors, the autophagic pathway is likely poised to counter infection or cancer as a "fail-safe" mechanism of non-apoptotic cell death.

REFERENCES

The contents of the references discussed herein are hereby incorporated by reference herein for all purposes.

1. M. O. Hengartner, H. R. Horvitz, *Current Opinion in Genetics & Development* 4, 581-6 (1994).
2. A. Degterev, M. Boyce, J. Yuan, *Oncogene* 22, 8543-67 (2003).
3. D. W. Nicholson, N. A. Thornberry, *Science* 299, 214-5 (2003).
4. A. Strasser, L. O'Connor, V. M. Dixit, *Annual Review of Biochemistry* 69, 217-45 (2000).
5. M. Leist, M. Jaattela, *Nature Reviews Molecular Cell Biology* 2, 589-98 (2001).
6. F. K. Chan, J. Shisler, J. G. Bixby, M. Felices, L. Zheng, M. Appel, J. Orenstein, B. Moss, M. J. Lenardo, *J Biol Chem.* 278, 51613-21 (2003).
7. N. Holler et al., *Nature Immunology* 1, 489-95 (2000).
8. Y. Ohsumi, *Nature Reviews Molecular Cell Biology* 2, 211-6 (2001).
9. D. J. Klionsky, S. D. Emr, *Science* 290, 1717-21 (2000).
10. E. H. Baehrecke, *Nature Reviews Molecular Cell Biology* 3, 779-87 (2002).
11. W. Fiers, R. Beyaert, W. Declercq, P. Vandenabeele, *Oncogene* 18, 7719-30 (1999).
12. P. G. Clarke, *Anatomy & Embryology* 181, 195-213 (1990).
13. S. M. Gorski, et al. *Current Biology* 13, 358-63 (2003).
14. C. Y. Lee et al., *Current Biology* 13, 350-7 (2003).
15. L. Jia et al., *British Journal of Haematology* 98, 673-85 (1997).
16. I. Tanida, N. Mizushima, M. Kiyooka, M. Ohsumi, T. Ueno, Y. Ohsumi, E. Kominami, *Mol Biol Cell.* 10, 1367-79 (1999).
17. J. Kim, V. M. Dalton, K. P. Eggerton, S. V. Scott, D. J. Klionsky, *Mol Biol Cell.* 10, 1337-51 (1999).
18. X. H. Liang et al., *Journal of Virology* 72, 8586-96 (1998).
19. X. H. Liang et al., *Nature* 402, 672-6 (1999).
20. Z. Yue, S. Jin, C. Yang, A. J. Levine, N. Heintz, *Proceedings of the National Academy of Sciences of the United States of America* 100, 15077-82 (2003).
21. X. Qu et al., *J Clin Invest.* 112, 1809-20 (2003).
22. A. Devin, Y. Lin, Z. G. Liu, *EMBO Rep.* 4, 623-7 (2003).
23. L., Yu, P. Dutt, M. J. Lenardo, unpublished data
24. H. J. Chun et al., *Nature* 419, 395-9 (2002).28.
25. Y. Lin, A. Devin, Y. Rodriguez, Z. G. Liu, *Genes & Development* 13, 2514-26 (1999).
26. K. R. Mills, M. Reginato, J. Debnath, B. Queenan, J. S. Brugge, *Proceedings of the National Academy of Sciences of the United States of America* 101, 3438-43 (2003).
27. M. Li et al., *Science* 288, 335-9 (2000).
28. J. Yuan, M. Lipinski, A. Degterev, *Neuron* 40, 401-13 (2003).
29. B. Levine, D J. Klionsky, *Dev. Cell* 6, 463-477 (2004).
30. M. Tsukada, Y. Ohsumi, *FEBS Letters* 333, 169-74 (1993).
31. M. Thumm, R. Egner, B. Koch, M. Schlumpherger, M. Straub, et al. *FEBS Letters* 349, 275-280 (1994).

32. T. M. Harding, K A Morano, S V Scott, et al., *J. Cell Biol.* 131, 591-602 (1995).
33. D J. Klionsky, J M Cregg, W A J Dunn, S D Ernt, et al. *Dev Cell* 5, 539-45 (2003).
34. J U. Schweichel, H J. Merket, *Teratology* 7, 253-66 (1973).
35. PGH. Clarke, *Anat. Embryol* 181, 195-213 (1990).
36. M. Chautan, G. Chazal, F. Cecconi, P. Gruss, et al., *Curr. Biol.* 9, 967-70 (1990)
37. R W. Oppenheim, R A Flavell, S. Vinsant, et al., *J. Neutosci.* 21, 4752-60 (2001).

That which is claimed is:

1. A composition comprising a caspase-8 inhibitor comprising antibodies that specifically bind caspase-8 and wherein the composition further comprises at least one polynucleotide sequence encoding a polypeptide which is selected from ATG6, ATG7, Beclin-1, HsGSA7, mAPG7, and APG6.

2. A composition comprising a caspase-8 inhibitor comprising antibodies that specifically bind caspase-8 and wherein the composition further comprises at least one polynucleotide sequence comprising SEQ ID NO: 1, SEQ ID NO: 3, SEQ ID NO: 18, or SEQ ID NO: 20.

* * * * *

UNITED STATES PATENT AND TRADEMARK OFFICE
CERTIFICATE OF CORRECTION

PATENT NO. : 7,838,645 B2  
APPLICATION NO. : 11/119569  
DATED : November 23, 2010  
INVENTOR(S) : Eric H. Baehrecke Page 1 of 1

It is certified that error appears in the above-identified patent and that said Letters Patent is hereby corrected as shown below:

On the cover page, left column, lines 11-12, "National Institutes of Health" should be --The United States of America, as represented by the Secretary, Department of Health and Human Services--

Signed and Sealed this

Eleventh Day of January, 2011

David J. Kappos
*Director of the United States Patent and Trademark Office*